United States Patent [19]

Beck et al.

[11] Patent Number: 5,071,865
[45] Date of Patent: Dec. 10, 1991

[54] PESTICIDAL 2-ACYLAMINO-4-HALOGENO-5-NITRO-THIAZOLES

[75] Inventors: Gunther Beck, Leverkusen; Stefan Dutzmann, Duesseldorf; Wilhelm Brandes, Leichlingen; Wilfried Paulus, Krefeld, all of Fed. Rep. of Germany

[73] Assignee: Bayer Aktiengesellschaft, Leverkusen, Fed. Rep. of Germany

[21] Appl. No.: 532,281

[22] Filed: Jun. 1, 1990

[30] Foreign Application Priority Data

Jun. 14, 1989 [DE] Fed. Rep. of Germany ....... 3919365

[51] Int. Cl.$^5$ .................... C07D 307/71; A01N 43/78
[52] U.S. Cl. .................................. 514/370; 514/342; 546/280; 548/181; 548/192
[58] Field of Search ................ 548/192, 181; 514/370, 514/342; 546/280

[56] References Cited

U.S. PATENT DOCUMENTS

| 2,839,523 | 6/1958 | Towne et al. ...................... 514/370 |
| 2,852,504 | 9/1958 | Towne et al. ...................... 514/370 |
| 4,962,102 | 10/1990 | Beck ................................... 514/212 |

FOREIGN PATENT DOCUMENTS

| 0031563 | 7/1981 | European Pat. Off. . |
| 8800944 | 8/1986 | European Pat. Off. . |
| 3030661 | 1/1982 | Fed. Rep. of Germany . |
| 3101889 | 8/1982 | Fed. Rep. of Germany . |
| 3518520 | 11/1986 | Fed. Rep. of Germany . |
| 2435905 | 4/1980 | France . |

OTHER PUBLICATIONS

Chemical Abstracts, vol. 107, No. 21, Nov. 23, 1987, 1-Pharmacology.
R. Wegler, "Chemie der Pflanzenschutz-und Schädlingsbekämpfungsmittel", vol. 2, p. 124, article.
R. Wegler, "Chemie der Pflanzenschutz-und Schädlingsbekämpfungsmittel", vol. 3, p. 292, article.

*Primary Examiner*—Robert Gerstl
*Attorney, Agent, or Firm*—Sprung Horn Kramer & Woods

[57] ABSTRACT

Pesticidal 2-acylamino-4-halogeno-5-nitrothiazoles of the formula

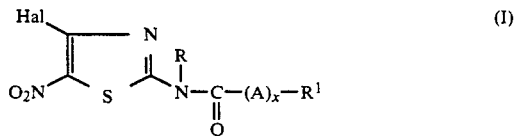

in which
Hal represents halogen,
x represents an integer 0 or 1,
A represents O, S or N—R$^2$, where
R$^2$ represents hydrogen, alkyl, alkenyl, halogenoalkyl, cyanoalkyl or alkoxycarbonylalkyl, or represents cycloalkyl, aryl or aralkyl, each of which is optionally monosubstituted to polysubstituted by identical or different substituents, and
R and R$^1$ each independently represents hydrogen or various organic radicals, with the exception that R$^1$ is not hydrogen when A represents O or S, and the compound 2-acetylamino-4-iodo-5-nitro-thiazole is excepted.

20 Claims, No Drawings

PESTICIDAL 2-ACYLAMINO-4-HALOGENO-5-NITRO-THIAZOLES

The present invention relates to new 2-acylamino-4-halogeno-5-nitrothiazole derivatives, to several processes for their preparation, to their use in pesticides and to some new intermediates.

It is known that thiazoles which are substituted by, for example, hydroxyphenoxy, are employed in medicine for the treatment of tumors (cf. WO 88/00944).

Furthermore, it is known that 2,4-dichloro-5-nitrothiazole has a microbicidal, above all fungicidal, action in plant protection (cf. DE-OS (German Published Specification) 3,518,520).

Thiazole derivatives, such as, for example, 4,5-dichloro-2-propinyloxy-thiazole, are also known as synergists (cf. DE-OS (German Published Specification) 3,030,661).

Furthermore, 2-acetamino-4-iodo-5-nitrothiazole, inter alia, is known as a starting material for 2-amino-4-alkylsulphonyl-5-nitrothiazole-azo derivatives which are used as dyes (cf. US 2,852,504 and US 2,839,523).

Furthermore, phenoxycarboxamides are known which can, inter alia, also contain a thiazole radical. These compounds are known as herbicides (cf. DE-OS (German Published Specification) 3,101,889).

Furthermore, it is known that certain substituted thiazoles, such as, for example, 4-benzimidazol-2-ylthiazole (thiabendazol) are used as fungicides in the protection of materials (cf., for example, R. Wegler "Chemie der Pflanzenschutz und Schädlingsbekämpfungsmittel [Chemistry of Plant Protection Agents, and Pesticides]", Vol. 2, p. 124 and Vol. 3, p. 292; Springer Verlag, Berlin, Heidelberg, N.Y. 1970).

However, the range of action of these previously known compounds is not complete, and the microbicidal activity is not always satisfactory in certain fields of indication.

New 2-acylamino-4-halogeno-5-nitrothiazole derivatives have been found, of the formula (I)

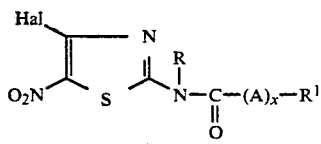

in which
Hal represents halogen,
x represents an integer 0 or 1,
A represents O, S or N—$R^2$, where
$R^2$ represents hydrogen, alkyl, alkenyl, halogenoalkyl, cyanoalkyl or alkoxycarbonylalkyl, or represents cycloalkyl, aryl or aralkyl, each of which is optionally monosubstituted to polysubstituted by identical or different substituents,
R represents hydrogen, alkyl, alkenyl or alkinyl, it being possible for each of the abovementioned radicals to be optionally monosubstituted to polysubstituted by identical or different substituents from the series comprising halogen, alkoxy, aryloxy, alkylmercapto, arylmercapto and cyano, or R represents cycloalkyl which is optionally monosubstituted to polysubstituted by identical or different alkyl substituents, it being possible, in addition to the alkyl substitution, for a ring to be fused on, or R represents aralkyl which is optionally monosubstituted to polysubstituted in the aryl moiety by identical or different substituents from the series comprising halogen, alkyl, halogenoalkyl, nitro, alkoxy, alkylmercapto and cyano, or R represents aryl which is optionally monosubstituted to polysubstituted by identical or different substituents from the series comprising halogen, alkyl, alkenyl, alkinyl, halogenoalkyl, nitro, alkoxy, alkylmercapto, dialkylamino, carbalkoxy, carbamoyl, N-alkylcarbamoyl, N,N-dialkylcarbamoyl, halogenoalkyloxy, halogenoalkylmercapto, alkylsulphonylamino, alkylsulphonyl, aryl, aryloxy, arylmercapto, acyloxy, acyl, sulphamoyl, N-alkylsulphamoyl, N-acyl-N-alkylsulphamoyl, N,N-dialkylsulphamoyl, aralkyloxy, aralkylmercapto, acylamino, acylaminosulphonyl, acylalkylamino, cycloalkyl and cyano, and $R^1$ represents hydrogen, alkyl, alkenyl, alkinyl, halogenoalkyl, cyanoalkyl or alkoxycarbonylalkyl, or represents cycloalkyl, aryl, heteroaryl, aralkyl or heteroaralkyl, each of which is optionally monosubstituted to polysubstituted by identical or different substituents, or R and $R^1$ together with the group —N—CO—(A)$_x$—at which they are located, form a ring which can optionally be interrupted by one or more further identical or different hetero atoms and which can optionally be monosubstituted to polysubstituted by identical or different substituents, or $R^1$ and $R^2$ together with the nitrogen atom at which they are located form a ring which can optionally be interrupted by one or more further identical or different hetero atoms and which can optionally be monosubstituted to polysubstituted by identical or different substituents, and further rings can optionally be fused on, with the exception that $R^1$ is not hydrogen when A represents O or S, and the compound 2-acetylamino-4-iodo-5-nitro-thiazole is excepted.

Furthermore, it has been found that the 2-acylamino-4-halogeno-5-nitrothiazole derivatives of the formula (I)

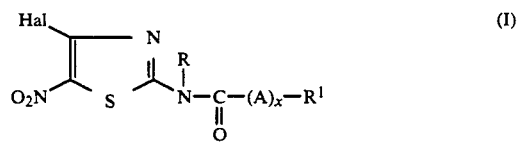

in which
Hal represents halogen,
x represents an integer 0 or 1,
A represents O, S or N—$R^2$, where
$R^2$ represents hydrogen, alkyl, alkenyl, halogenoalkyl, cyanoalkyl or alkoxycarbonylalkyl, or represents cycloalkyl, aryl or aralkyl, each of which is optionally monosubstituted to polysubstituted by identical or different substituents,
R represents hydrogen, alkyl, alkenyl or alkinyl, it being possible for each of the abovementioned radicals to be optionally monosubstituted to polysubstituted by identical or different substituents from the series comprising halogen, alkoxy, aryloxy, alkylmercapto, arylmercapto and cyano, or R represents cycloalkyl which is optionally monosubstituted to polysubstituted by identical or different alkyl substituents, it being possible, in addition to the alkyl substitution, for a ring to be fused on, or R represents aralkyl which is optionally monosubstituted to polysubstituted in the aryl moiety by identical or different substituents from the series comprising halogen, alkyl, halogenoalkyl, nitro, alkoxy, alkylmercapto and cyano, or R represents aryl which is optionally monosubstituted to polysubstituted by identical or different substituents from the series comprising halogen, alkyl, alkenyl, alkinyl, halogenoalkyl, nitro, alkoxy, alkylmercapto, dialkylamino, carbalkoxy, carbamoyl, N-alkylcarbamoyl, N,N-dialkylcarbamoyl, halogenoalkyloxy, halogenoalkylmercapto, alkylsulphonylamino, alkylsulphonyl, aryl, aryloxy, arylmercapto, acyloxy, acyl, sulphamoyl, N-alkylsulphamoyl, N-acyl-N-alkylsulphamoyl, N,N-dialkylsulphamoyl, aralkyloxy, aralkylmercapto, acylamino, acylaminosulphonyl, acylalkylamino, cycloalkyl and cyano, and $R^1$ represents hydrogen, alkyl, alkenyl, alkinyl, halogenoalkyl, cyanoalkyl or alkoxycarbonylalkyl, or represents cycloalkyl, aryl, heteroaryl, aralkyl or heteroaralkyl, each of which is optionally monosubstituted to polysubstituted by identical or different substituents, or R and $R^1$ together with the group —N—CO—(A)$_x$— at which they are located, form a ring which can optionally be interrupted by one or more further identical or different hetero atoms and which can optionally be monosubstituted to polysubstituted by identical or different substituents, or $R^1$ and $R^2$ together with the nitrogen atom at which they are located form a ring, which can optionally be interrupted by one or more further identical or different hetero atoms and which can optionally be monosubstituted to polysubstituted by identical or different substituents, and further rings can optionally be fused on, with the exception that $R^1$ is not hydrogen when A represents O or S, are obtained when a) 2,4-dihalogeno-5-nitrothiazoles of the formula (II)

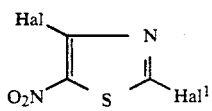   (II)

in which

Hal$^1$ represents halogen,

Hal is as defined above and

Hal and Hal$^1$ can be identical or different, are reacted with nucleophiles of the formula (III)

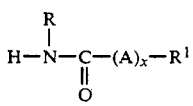   (III)

in which

A, x, R and $R^1$ are as defined above, or their metal salts, if appropriate in the presence of acid-binding agents and in the presence of diluents, or b) 2-amino-4-halogeno-5-nitrothiazole derivatives of the formula (IV)

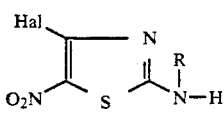   (IV)

in which

Hal and R are as defined above, are reacted with halogenocarbonyl compounds of the formula (V)

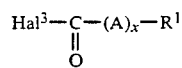   (V)

in which

Hal$^3$ represents halogen and A, X and $R^1$ are as defined above, if appropriate in the presence of acid-binding agents and in the presence of diluents, or c) in the event that x represents O and $R^1$ is as defined above, hydrogen being excepted, 2-amino-4-halogeno-5-nitrothiazole derivatives of the formula (IV) are reacted with carboxylic anhydrides of the formula (VI)

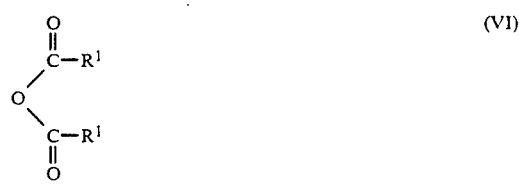   (VI)

in which $R^1$ is as defined above, hydrogen being excepted, if appropriate in the presence of diluents, or d) in the event that x represents 1 and A represents NH, 2-amino-4-halogeno-5-nitrothiazole derivatives of the formula (IV) are reacted with isocyanates of the formula (VII)

$$O=C=N-R^1 \quad (VII)$$

in which $R^1$ is as defined above, hydrogen being excepted, if appropriate in the presence of diluents, or e) in the event that x represents 1 and A is as defined above, 4-halogeno-2-halogenocarbonylamino-5-nitrothiazole derivatives of the formula (VIII)

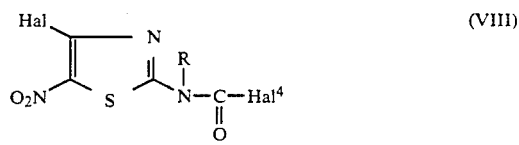   (VIII)

in which

Hal$^4$ represents halogen,

Hal is as defined above and

Hal and Hal$^4$ can be identical or different and

R is as defined above, hydrogen being excepted, are reacted with nucleophiles of the formula (IX)

$$H-(A)_2-R^1 \quad (IX)$$

in which x represents 1 and $R^1$ and A are as defined above, or their metal salts, if appropriate in the presence of acid-binding agents and in the presence of diluents.

Finally, it has been found that the new 2-acylamino-4-halogeno-5-nitrothiazole derivatives of the formula (I)

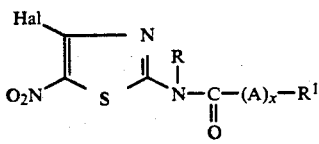

in which
Hal represents halogen,
x represents an integer 0 or 1,
A represents O, S or N—$R^2$, where
$R^2$ represents hydrogen, alkyl, alkenyl, halogenoalkyl, cyanoalkyl or alkoxycarbonylalkyl, or represents cycloalkyl, aryl or aralkyl, each of which is optionally monosubstituted to polysubstituted by identical or different substituents,
R represents hydrogen, alkyl, alkenyl or alkinyl, it being possible for each of the abovementioned radicals to be optionally monosubstituted to polysubstituted by identical or different substituents from the series comprising halogen, alkoxy, aryloxy, alkylmercapto, arylmercapto and cyano, or R represents cycloalkyl which is optionally monosubstituted to polysubstituted by identical or different alkyl substituents, it being possible, in addition to the alkyl substitution, for a ring to be fused on, or R represents aralkyl which is optionally monosubstituted to polysubstituted in the aryl moiety by identical or different substituents from the series comprising halogen, alkyl, halogenoalkyl, nitro, alkoxy, alkylmercapto and cyano, or R represents aryl which is optionally monosubstituted to polysubstituted by identical or different substituents from the series comprising halogen, alkyl, alkenyl, alkinyl, halogenoalkyl, nitro, alkoxy, alkylmercapto, dialkylamino, carbalkoxy, carbamoyl, N-alkylcarbamoyl, N,N-dialkylcarbamoyl, halogenoalkyloxy, halogenoalkylmercapto, alkylsulphonylamino, alkylsulphonyl, aryl, aryloxy, arylmercapto, acyloxy, acyl, sulphamoyl, N-alkylsulphamoyl, N-acyl-N-alkylsulphamoyl, N,N-dialkylsulphamoyl, aralkyloxy, aralkylmercapto, acylamino, acylaminosulphonyl, acylalkylamino, cycloalkyl and cyano, and
$R^1$ represents hydrogen, alkyl, alkenyl, alkinyl, halogenoalkyl, cyanoalkyl or alkoxycarbonylalkyl, or represents cycloalkyl, aryl, heteroaryl, aralkyl or heteroaralkyl, each of which is optionally monosubstituted to polysubstituted by identical or different substituents, or
R and $R^1$ together with the group —N—CO—$(A)_x$—at which they are located, form a ring which can optionally be interrupted by one or more further identical or different hetero atoms and which can optionally be monosubstituted to polysubstituted by identical or different substituents, or
$R^1$ and $R^2$ together with the nitrogen atom at which they are located form a ring which can optionally be interrupted by one or more further identical or different hetero atoms and which can optionally be monosubstituted to polysubstituted by identical or different substituents, and further rings can optionally be fused on, with the exception that $R^1$ is not hydrogen when A represents O or S, have a powerful action against pests, above all against fungi in the plant sector and against microbes in industrial materials.

Within the context of the present invention, the substituents are as defined above; some substituents may be mentioned specifically here.

Unless otherwise defined, halogen can denote fluorine, chlorine, bromine and iodine.

In this context, alkyl in R generally represents a straight-chain or branched hydrocarbon radical having 1 to 12 carbon atoms. Examples which may be mentioned are methyl, ethyl, propyl, isopropyl, butyl, isobutyl, t-butyl, pentyl, isopentyl, hexyl, isohexyl, isoheptyl, octyl and isooctyl.

Alkenyl or alkinyl in R generally represent a straight-chain or branched hydrocarbon radical, each of which has up to 12 carbon atoms and one or more, preferably one or two, double bonds or triple bonds, respectively. Examples which may be mentioned are allyl, propenyl, isopropenyl, butenyl, isobutenyl, pentenyl, isopentenyl, hexenyl, isohexenyl, heptenyl, isoheptenyl, octenyl, isooctenyl, propinyl, butinyl, pentinyl, isopentinyl, hexinyl and octinyl.

Cycloalkyl in R generally represents a cyclic hydrocarbon radical having 3 to 8 carbon atoms. The cyclopropyl, cyclopentyl and, cyclohexyl ring are preferred. Examples which may be mentioned are cyclopropyl, cyclopentyl, cyclohexyl, cycloheptyl and cyclooctyl.

Halogenoalkyl in R generally represents straight-chain or branched lower alkyl having 1 to 8 carbon atoms and one to more, preferably 1 to 10, identical or different halogen atoms. The following may be mentioned by way of example: fluoromethyl, chloromethyl, bromomethyl, fluoroethyl, chloroethyl, bromoethyl, fluoropropyl, chloropropyl, bromopropyl, fluorobutyl, chlorobutyl, bromobutyl, fluoroisopropyl, chloroisopropyl, bromoisopropyl, difluoromethyl, trifluoromethyl, dichloromethyl, trichloromethyl, difluoroethyl, dichloroethyl, trifluoroethyl, tetrafluoroethyl, pentafluoroethyl, trichloroethyl and trifluoropropyl. Trifluoromethyl, difluoromethyl, fluoromethyl, chloromethyl and trifluoroethyl are very particularly preferred.

Halogenoalkenyl or halogenoalkinyl in R generally represents straight-chain or branched alkenyl or alkinyl, respectively, having up to 8 carbon atoms and 1 to 10, identical or different halogen atoms and one or more double bonds or triple bonds, respectively. Radicals having one double bond or triple bond are preferred. The following may be mentioned by way of example: 2,2-dichlorovinyl, 1,2,2-trichlorovinyl, chloropropinyl, etc.

Aryl can represent an aromatic hydrocarbon radical having 6 to 12 carbon atoms. Phenyl or naphthyl may be mentioned by way of example.

Aralkyl can represent a radical having 7 to 16 carbon atoms, it being possible for a straight-chain or branched alkyl radical having 1 to 4 carbon atoms to be substituted by an aromatic radical having 6 to 12 carbon atoms. Examples which may be mentioned are benzyl, phenylethyl and phenylpropyl. Benzyl and phenylethyl are preferred.

The aryl or aralkyl radicals can optionally be monosubstituted to polysubstituted, preferably monosubstituted to pentasubstituted, by identical or different substituents.

Alkoxyalkyl and alkylmercaptoalkyl generally represent a straight-chain or branched hydrocarbon radical which has 1 to 4 carbon atoms per alkyl or alkoxy and alkylthio moiety, respectively, and which is bonded via oxygen or sulphur, respectively. Examples which may be mentioned are methoxymethyl, methoxyethyl, methoxypropyl, methoxybutyl, ethoxymethyl, ethoxyethyl, ethoxypropyl, ethoxybutyl, propoxymethyl, propoxyethyl, propoxypropyl, propoxybutyl, butoxymethyl, butoxyethyl, butoxypropyl and butoxybutyl.

Preferred are methylthiomethyl, methylthioethyl, methylthiopropyl, methylthiobutyl, ethoxythiomethyl, ethylthioethyl, ethylthiopropyl, ethylthiobutyl, propylthiomethyl, propylthioethyl, propylthiopropyl, propylthiobutyl, butylthiomethyl, butylthioethyl, butylthiopropyl and butylthiobutyl.

In general, it holds true that aliphatic radicals, such as, for example, alkyl, alkoxy, alkoxycarbonyl etc. can always be straight-chain or branched.

As far as substitution of rings, such as phenyl, naphthyl, heterocycles etc. is concerned, it holds true that they can generally be monosubstituted to pentasubstituted, particularly preferably monosubstituted to trisubstituted, by identical or different substituents, unless otherwise indicated.

Formula (I) provides a general definition of the 2-acylamino-4-halogeno-5-nitrothiazole derivatives according to the invention. Preferred compounds of the formula (I) are those in which Hal represents chlorine, bromine or iodine, x represents an integer 0 or 1, represents O, S or NR$^2$, where R$^2$ represents hydrogen, alkyl having 1 to 4 carbon atoms, alkenyl having 3 to 5 carbon atoms, halogenoalkyl having 1 to 3 carbon atoms and 1 to 5 identical or different halogen atoms, or represents cyanoalkyl having 1 or 2 carbon atoms in the alkyl moiety, or represents alkoxycarbonylalkyl having 1 to 4 carbon atoms in each the alkoxy and alkyl moiety, or represents cycloalkyl having 3 to 6 carbon atoms, or represents phenyl or phenylalkyl, each of which is optionally monosubstituted to trisubstituted by identical or different substituents from the series comprising alkyl having 1 to 4 carbon atoms, fluorine, chlorine, bromine or alkoxy having 1 to 4 carbon atoms, where phenylalkyl has 1 to 3 carbon atoms in the alkyl moiety, and R represents hydrogen, alkyl having 1 to 12 carbon atoms, alkenyl having up to 12 carbon atoms, alkinyl having up to 12 carbon atoms, or halogenoalkyl, halogenoalkenyl or halogeno,alkinyl, each of which has up to 8 carbon atoms and 1 to 10 identical or different halogen atoms, or represents alkoxyalkyl, alkylmercaptoalkyl or cyanoalkyl, each of which has 1 to 4 carbon atoms per alkyl, alkoxy or alkylthio moiety, respectively, or represents phenyloxyalkyl or phenylmercaptoalkyl, each of which has 1 to 4 carbon atoms in the alkyl moiety, it being possible for the phenyl radicals to be optionally monosubstituted to trisubstituted by identical or different substituents from the series comprising fluorine, chlorine, bromine or alkyl having 1 to 4 carbon atoms, or represents cycloalkyl which has 3 to 8 carbon atoms and which is optionally monosubstituted to trisubstituted by identical or different alkyl substituents having 1 to 4 carbon atoms, it being possible for the cycloalkyl ring to additionally contain a fused-on ring, or represents phenylalkyl which has 1 to 4 carbon atoms in the alkyl moiety and which is optionally monosubstituted to pentasubstituted by identical or different substituents from the series comprising halogen, alkyl having 1 to 4 carbon atoms, halogenoalkyl having 1 to 4 carbon atoms and 1 to 8 identical or different halogen atoms, nitro, cyano, alkoxy having 1 to 4 carbon atoms or alkylmercapto having 1 to 4 carbon atoms, it being possible for the alkyl moiety to optionally contain a further phenyl radical as a substituent which can optionally also be substituted as described above, or represents phenyl which is optionally monosubstituted to pentasubstituted by identical or different substituents from the series comprising halogen, nitro, alkenyl or alkinyl, in each case having up to 5 carbon atoms, alkyl, alkoxy, alkylmercapto, carbalkoxy, alkylsulphonylamino, alkylsulphonyl, sulphamoyl, N-alkylsulphamoyl, N,N-dialkylsulphamoyl, dialkylamino, carbamoyl, N-alkylcarbamoyl or N,N-dialkylcarbamoyl, in each case having 1 to 4 carbon atoms per alkyl radical, halogenoalkyl, halogenoalkoxy or halogenoalkylmercapto, in each case having 1 to 4 carbon atoms and 1 to 8 identical or different halogen atoms per listed radical, phenyl, phenoxy, phenylmercapto, acyloxy having 1 to 3 carbon atoms, acyl having 1 to 3 carbon atoms, phenylalkyloxy having 1 to 3 carbon atoms in the alkyl moiety, phenylalkylmercapto having 1 to 3 carbon atoms, acylamino having 1 to 3 carbon atoms, acylalkylamino, N-acylalkylsulphamoyl or acylaminosulphonyl, in each case having 1 to 3 carbon atoms per acyl and alkyl radical, cycloalkyl having 4 to 6 carbon atoms and cyano, or represents naphthyl, R$^1$ represents hydrogen, alkyl having 1 to 6 carbon atoms, alkenyl or alkinyl, in each case having 3 to 5 carbon atoms, halogenoalkyl having 1 to 5 carbon atoms and 1 to 8 identical or different halogen atoms, cyanoalkyl having 1 or 2 carbon atoms in the alkyl moiety, alkoxycarbonylalkyl having 1 to 4 carbon atoms in each the alkoxy and alkyl moiety, or represents cycloalkyl which has 3 to 6 carbon atoms and which is optionally monosubstituted to trisubstituted by alkyl having 1 to 3 carbon atoms, or represents phenyl or phenylalkyl, each of which is optionally monosubstituted to trisubstituted by identical or different alkyl substituents having 1 to 4 carbon atoms or by fluorine, chlorine, bromine, alkoxy, halogenoalkyl or halogenoalkoxy, in each case having 1 to 4 carbon atoms and where appropriate 1 to 5 identical or different halogen atoms, where phenylalkyl has 1 to 3 carbon atoms in the alkyl moiety, or R: represents heterocyclyl or heterocyclylalkyl, each of which has 1 to 4 carbon atoms in the alkyl moiety and 5 to 7 ring members in the heterocyclyl moiety which can contain one to three identical or different hetero atoms, for example oxygen, sulphur or nitrogen, and to which further rings may be fused, it being possible for each of the rings to be optionally monosubstituted to trisubstituted by identical or different substituents from the series comprising halogen, alkyl having 1 to 4 carbon atoms and alkoxy, having 1 to 3 carbon atoms, or R and R$^1$ together with the group —N—CO—(A)$_x$—, at which they are located form a ring which has 5 to 7 ring members and which can optionally contain one or two further nitrogen and/or oxygen atoms and which can optionally be monosubstituted to trisubstituted by alkyl having 1 to 4 carbon atoms, or R and R$^2$ together with the nitrogen atom at which they are located form a ring which has 5 to 7 ring members and which can optionally contain one or two further nitrogen and/or oxygen atoms and which can optionally be monosubstituted to trisubstituted by alkyl having 1 to 4 carbon atoms and where further rings can be fused on, with the exception that R$^1$ is not hydrogen when A represents O or S, and the compound 2-acetylamino-4-iodo-5-nitro-thiazole being excepted.

Particularly preferred compounds of the formula (I) are those in which

Hal represents chlorine, x represents 0,

R represents hydrogen, straight-chain or branched alkyl having 1 to 6 carbon atoms, straight-chain or branched alkenyl having up to 6 carbon atoms, halogenoalkyl having 1 to 4 carbon atoms and 1 to 6 identical or different halogen atoms, alkoxyalkyl having in each case 1 to 3 carbon atoms in each alkoxy or alkyl moiety, R furthermore represents cyclohexyl, naphthyl, phenylalkyl which has 1 to 4 carbon atoms in the straight-chain or branched alkyl moiety and which is optionally monosubstituted to trisubstituted by identical or different substituents from the series comprising alkyl having 1 to 3 carbon atoms and halogen, or represents phenyl which is optionally monosubstituted to pentasubstituted by identical or different alkyl substituents having 1 to 3 carbon atoms or which is optionally monosubstituted to trisubstituted by identical or different substituents from the series comprising halogen, nitro, cyclohexyl, alkyl, having 1 to 4 carbon atoms, alkoxy having 1 to 4 carbon atoms, alkylsulphonyl having 1 to 4 carbon atoms, dialkylamino having 1 to 4 carbon atoms per alkyl moiety, carbamoyl, N-alkylcarbamoyl or N,N-dialkyl-carbamoyl, each of which has 1 to 4 carbon atoms per alkyl moiety, halogenoalkoxy or halogenoalkylmercapto, in each case having 1 to 4 carbon atoms and 1 to 5 identical or different halogen atoms, acyl or acylamino, in each case having 1 to 3 carbon atoms, acyloxy having 1 to 3 carbon atoms, and N-acyl-alkylsulphamoyl or acylaminosulphonyl, in each case having 1 to 3 carbon atoms per acyl and alkyl moiety, and $R^1$ represents alkyl having 1 to 6 carbon atoms, halogenoalkyl having 1 to 3 carbon atoms and 1 to 5 identical or different halogen atoms, or represents cyclohexyl which is optionally monosubstituted to trisubstituted by methyl, ethyl or propyl, or represents phenyl which is optionally monosubstituted to trisubstituted in each case by identical or different substituents from the series comprising alkyl having 1 to 3 carbon atoms fluorine, chlorine, bromine, alkoxy, halogenoalkyl or halogenoalkoxy having 1 to 3 carbon atoms in each case and where appropriate 1 to 5 identical or different halogen atoms, or R represents a 5- or 6-membered ring which has 1 to 3 identical or different hetero atoms, such as nitrogen, sulphur or oxygen, and which is optionally monosubstituted to trisubstituted by identical or different substituents from the series comprising chlorine, methyl, ethyl and n- or isopropyl, examples being oxazole, isoxazole, thiazole, imidazole, triazole, pyrazole, pyridine, morpholine and pyrazine.

Other particularly preferred compounds of the formula (I) are those in which:

R represents hydrogen, straight-chain or branched alkyl having 1 to 6 carbon atoms, straight-chain or branched alkenyl having up to 6 carbon atoms, halogenoalkyl having 1 to 4 carbon atoms and 1 to 6 identical or different halogen atoms, alkoxyalkyl in each case having 1 to 3 carbon atoms in each alkoxy and alkyl moiety, R furthermore represents cyclohexyl, naphthyl, phenylalkyl which has 1 to 4 carbon atoms in the straight-chain or branched alkyl moiety and which is optionally monosubstituted to trisubstituted by identical or different substituents from the series comprising alkyl having 1 to 3 carbon atoms and halogen, or represents phenyl which is optionally monosubstituted to pentasubstituted by identical or different alkyl substituents having 1 to 3 carbon atoms or which is optionally monosubstituted to trisubstituted by identical or different substituents from the series comprising halogen, nitro, cyclohexyl, alkyl having 1 to 4 carbon atoms, alkoxy having 1 to 4 carbon atoms, alkylsulphonyl having 1 to 4 carbon atoms, dialkylamino having 1 to 4 carbon atoms per alkyl moiety, carbamoyl, N-alkylcarbamoyl or N,N-dialkyl-carbamoyl having 1 to 4 carbon atoms per alkyl moiety, halogenoalkoxy or halogenoalkylmercapto„in each case having 1 to 4 carbon atoms and 1 to 5 identical or different halogen atoms, acyl or acylamino, in each case having 1 to 3 carbon atoms, acyloxy having 1 to 3 carbon atoms, and N-acyl-alkylsulphamoyl or acylaminosulphonyl, in each case having 1 to 3 carbon atoms per acyl and alkyl moiety, and x represents 1, A represents O or S and $R^1$ represents alkyl having 1 to 4 carbon atoms, or represents phenyl which is optionally monosubstituted to trisubstituted by identical or different substituents from the series comprising halogen, alkoxy, alkyl, halogenoalkyl and halogenoalkoxy, in each case having 1 to 3 carbon atoms and where appropriate 1 to 5 identical or different halogen atoms, or $R^1$ represents a 5- or 6-membered ring having 1 or 2 identical or different hetero atoms, such as nitrogen and oxygen, R and $R^1$ with the group —N—CO—(A)$_x$ — at which they are located form a 5- or 6- membered, ring which can optionally be monosubstituted to trisubstituted by identical or different substituents from the series comprising halogen and alkyl having 1 to 4 carbon atoms, examples being 2-keto-pyrrolidine and 2-ketopiperidine.

Other preferred compounds of the formula (I) are those in which

R represents hydrogen, straight-chain or branched alkyl having 1 to 6 carbon atoms, straight-chain or branched alkenyl having up to 6 carbon atoms, halogenoalkyl having 1 to 4 carbon atoms and 1 to 6 identical or different halogen atoms, alkoxyalkyl having in each case 1 to 3 carbon atoms in each alkoxy and alkyl moiety, R furthermore represents cyclohexyl, naphthyl, phenylalkyl which has 1 to 4 carbon atoms in the straight-chain or branched alkyl moiety and which is optionally monosubstituted to trisubstituted by identical or different substituents from the series comprising alkyl having 1 to 3 carbon atoms and halogen, or represents phenyl which is optionally monosubstituted to pentasubstituted by identical or different alkyl substituents having 1 to 3 carbon atoms or which is optionally monosubstituted to trisubstituted by identical or different substituents from the series comprising halogen, nitro, cyclohexyl, alkyl having 1 to 4 carbon atoms, alkoxy having 1 to 4 carbon atoms, alkylsulphonyl having 1 to 4 carbon atoms, dialkylamino having 1 to 4 carbon atoms per alkyl moiety, carbamoyl, N-alkyl-carbamoyl or N,N-dialkyl-carbamoyl having 1 to 4 carbon atoms per alkyl moiety, halogenoalkoxy or halogenoalkylmercapto, in each case having 1 to 4 carbon atoms and 1 to 5 identical or different halogen atoms, acyl or acylamino, in each case having 1 to 3 carbon atoms, acyloxy having 1 to 3 carbon atoms, or N-acyl-alkylsulphamoyl or acylaminosulphonyl, in each case having 1 to 3 carbon atoms per acyl and alkyl moiety, and x represents 1, A represents NR$^2$, $R^1$ represents hydrogen, alkyl having 1 to 6 carbon atoms, halogenoalkyl having 1 to 3 carbon atoms and 1 to 5 identical or different halogen atoms, or represents cyclohexyl which is optionally monosubstituted to trisubstituted by methyl, ethyl or propyl, or represents phenyl which is optionally monosubstituted to trisubstituted in each case by identical or different substituents from the series comprising alkyl having 1 to 3 carbon atoms, fluorine, chlorine, bromine, alkoxy, halogenoalkyl or halogenoalkoxy, in each case having 1 to 3 carbon atoms and where appropriate 1 to 5 identical or different halogen atoms, or represents a 5- or 6-membered ring which has 1 to 3 identical or different hetero atoms, such as nitrogen, sulphur or oxygen, and which is optionally monosubstituted to trisubstituted by identical or different substituents from the series comprising chlorine, methyl, ethyl and n- or isopropyl, $R^2$ represents hydrogen, alkyl having 1 to 4 carbon atoms, alkenyl having 3 to 5 carbon atoms, halogenoalkyl having 1 to 3 carbon atoms and 1 to 5 identical or different halogen atoms, or represents cyanoalkyl having 1 or 2 carbon atoms in the alkyl moiety, or represents cycloalkyl having 3 to 6 carbon atoms, or represents phenyl or phenylalkyl, each of which is optionally monosubstituted to trisubstituted by identical or different substituents from the series comprising alkyl having 1 to 4 carbon atoms, fluorine, chlorine, bromine or alkoxy having 1 to 4 carbon atoms, where phenylalkyl has 1 to 3 carbon atoms in the alkyl moiety, or $R^1$ and $R^3$ together with the nitrogen atom at which they are located form a ring having 5 to 7 ring members which can optionally contain one or two further nitrogen and/or oxygen atoms and which can optionally monosubstituted to trisubstituted by alkyl having 1 to 4 carbon atoms, and further rings can be fused on.

If, for example, 2,4-dichloro-5-nitrothiazole and N,N'-dimethylurea are used as starting substances in process (a) according to the invention, the course of the reaction can be represented by the following equation:

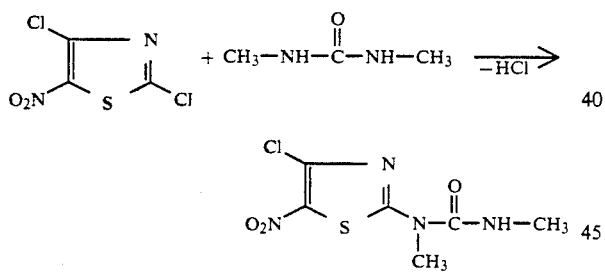

If, for example, 4-chloro-2-ethylamino-5-nitrothiazole and chloroacetyl chloride are used as starting substances, the course of process (b) according to the invention can be represented by the following equation:

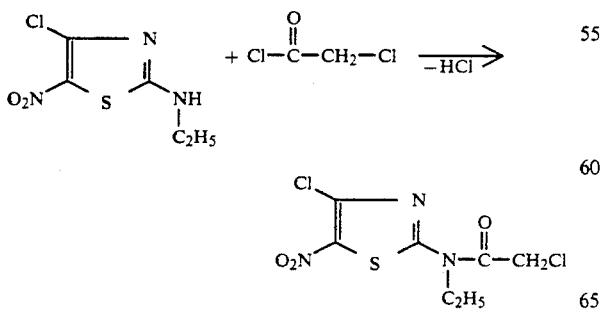

If, for example, 2-anilino-4-chloro-5-nitrothiazole and acetic anhydride are used as starting substances, the course of process (c) according to the invention can be represented by the following equation:

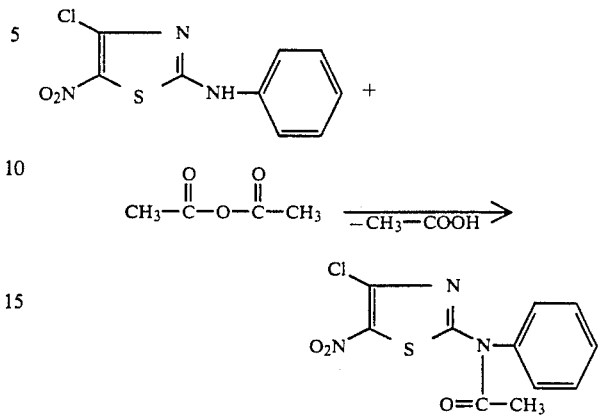

If, for example, 4-chloro-2-methylamino-5-nitrothiazole and phenyl isocyanate are used as starting substances, the course of process (d) according to the can be represented by the following equation:

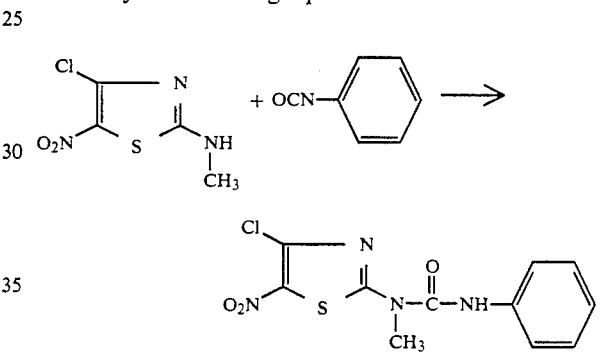

If, for example, 4-chloro-2-(N-chlorocarbonyl-N-methyl)-amino-5-nitrothiazole and methanol are used as starting substances, the course of process (e) according to the invention can be represented by the following equation:

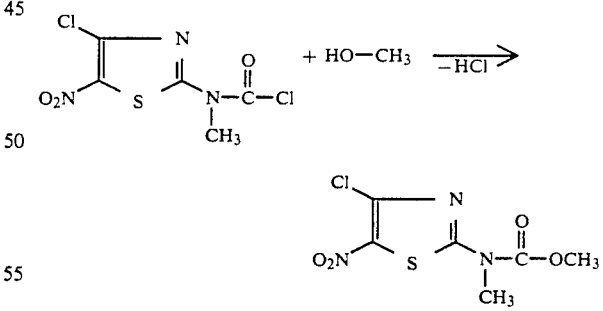

Some of the 2,4-dihalogeno-5-nitrothiazoles of the formula (II) which are required as starting materials in process (a) according to the invention are known, for example those compounds of the formula (II) in which Hal=Hal$^1$=bromine: Chem. Abstr. 61: 3087 f and in which Hal Hal$^1$ =chlorine, cf. DE-OS (German Published Specification) 3,518,520.

The two compounds which have been mentioned are producible for example by nitrating the corresponding 2,4-dihalogenothiazoles.

Compounds of the formula (II A)

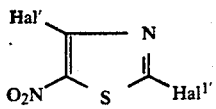

in which

Hal' and Hal¹' independently of one another represent chlorine, iodine or fluorine, with the proviso that the two Hal substituents must not simultaneously be chlorine, are the subject-matter of a German Appl.P 38 24 520.5, filed July 20, 1988, corresponding to U.S. Appl., S.N. 378,894 filed July 12, 1989, now pending. These substances also show a microbicidal action when used in the appropriate use concentrations.

Compounds of the formula (IIA) in which
Hal' = Hal¹' = iodine or
Hal' = chlorine and Hal¹ = iodine or
Hal' = iodine and Hal¹' = chlorine or
Hal' = chlorine and Hal¹' = fluorine, for example are new. Thus, the iodine compounds are obtained by reacting 2,4-dichloro-5-nitrothiazole with metal iodides, in particular sodium iodide, in lower aliphatic ketones, in particular acetone, as solvents, according to the following equations:

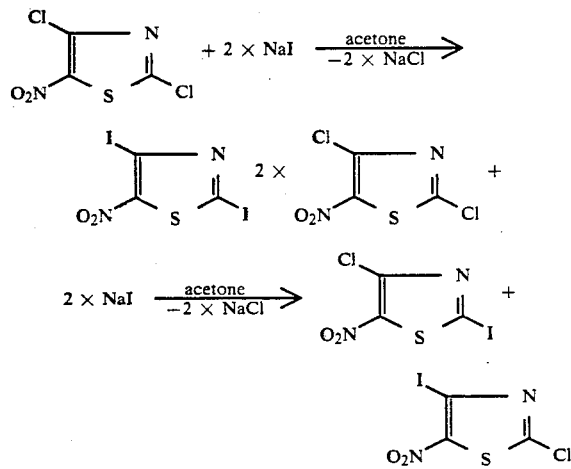

The two isomeric chloro-iodo-nitrothiazoles are formed beside each other and can be separated by fractional crystallization and/or by chromatographic methods. In general, the reaction temperature is between 0° C. and 130° C., preferably between 10° C. and 90° C.

Compounds of the formula (II A) in which at least one of the halogens is fluorine, for example Hal¹ = fluorine and Hal' = chlorine, that is to say, 4-chloro-2-fluoro-5-nitrothiazole, can be prepared by reacting 2,4-dichloro-5-nitrothiazole with metal fluorides, in particular sodium fluoride or potassium fluoride, in lower aliphatic nitriles, in particular in acetonitrile or propionitrile, as solvents in the presence of catalytic amounts of crown ethers, in particular of [18]crown-6. The reaction temperature is 0° C. to 50° C., preferably 10° C. to 30° C. The process is carried out using 2-15 moles of metal fluoride, preferably 3-12 moles of metal fluoride per mole of 2,4-dichloro-5-nitrothiazole.

The nucleophiles of the formula (III) which are furthermore required as starting materials in process (a) according to the invention ar basically known. In the event that specific compounds have not been described yet, they can h=prepared by known processes.

Suitable solvents for carrying out process (a) according to the invention are, in particular, aprotic, dipolar solvents, such as dimethylformamide, dimethylacetamide, N-methyl-2-pyrrolidinone, N-methylcaprolactam, tetramethylurea, N'N'-dimethyl-1,3-imidazolidin-2-one, hexamethylphosphoric trisamide, dimethyl sulphoxide, dimethyl sulphone and also tetramethylene sulphone (=sulpholane).

In process (a) according to the invention, the reaction temperature can be varied in wide ranges. In general, the process is carried out at between −20° C. and +150° C., preferably at 0° C. to 100° C.

As a rule, the reactions are carried out under atmospheric pressure, but they can also be carried out in closed vessels in which then a correspondingly higher pressure is established depending on the nature of the solvent and on the temperature.

In general, an acid-binding agent is required for binding the hydrogen halide which is liberated in process (a) according to the invention, as shown in the equation, but it is also possible to carry out the process without such an agent. Examples which can be used for this purpose are: alkali metal hydroxides, alkali metal carbonates or alkali metal hydrogen carbonates, or else alkali metal hydrides, preferably sodium hydride.

It is also possible to directly react metal salts, preferably alkali metal salts, of the particular nucleophile of the formula (III). The salts can be employed either as such or they can be prepared in situ, for example by adding alkali metal hydrides, preferably sodium hydride.

The aprotic, dipolar solvents dimethylformamide and N-methyl-2-pyrrolidinone are particularly preferred if the process is carried out without acid-binding agent. In contrast, if the process is carried out for example using sodium hydride, cyclic ethers, such as dioxane and tetrahydrofuran, are moreover particularly preferred as solvents.

In general, the reactants are reacted with each other in the stoichiometrically equimolar ratio.

Since the 2,4-dihalogeno-5-nitrothiazoles of the formula (II) carry a second halogen atom in the 4-position—which is, albeit, gradually markedly less reactive—, it is generally advantageous not to employ an excess of nucleophile of the formula (III) to exclude the formation of disubstitution products, which are undesirable in this case. It can therefore be advantageous in certain cases to employ an excess of 2,4-dihalogeno-5-nitrothiazole of the formula (II), which, in general, can be 20 to up to 100 mole %.

When carrying out process (a) according to the invention, it is preferred to initially introduce the 2,4-dihalogeno-5-nitrothiazole of the formula (II) into one of the mentioned solvents. If the process is carried out without acid-binding agent, the nucleophile of the formula (III) is then added at room temperature, and the mixture is heated to the desired final reaction temperature. If the process is carried out in the presence of an acid-binding agent—particularly preferably sodium hydride- , various procedures can be followed. Either the alkali salt of the nucleophile of the formula (III) is first produced in situ in a separate reaction vessel—preferably in a cyclic ether such as tetrahydrofuran—and it is then added at room temperature or below, preferably down to 0° C., to the solution of the 2,4-dihalogeno-5-nitrothiazole of the formula (II), or the nucleophile of the formula (III) can first be added to the solution of the 2,4-dihalogeno-5-nitrothiazole of the formula (II) and then—advantageously in portions - the acid-binding agent, particularly preferably sodium hydride, is added, or the acid-binding agent is added first and then—again, advantageously in portions—the nucleophile of the formula (III).

The mixture is then stirred at the desired reaction temperature until the reaction is complete.

The reaction products are isolated by customary methods. In the simplest case, some or all of the solvent may be distilled off in vacuo, and the reaction mixture is then stirred in excess ice-water, about the 5- to 10-fold volume of employed solvent, the mixture is filtered off, and the product is washed with water and dried. If the process was carried out using an excess of 2,4-dihalogeno-5-nitrothiazole, the latter can be dissolved out of the thoroughly dried crude product by stirring at room temperature with a solvent which dissolves virtually only the 2,4-dihalogeno-5-nitrothiazole of the formula (II), and, if appropriate, it can be reused in subsequent batches. An example which is particularly highly suitable in the case of 2,4-dichloro-5-nitrothiazole is petroleum ether. In the event that the reaction product, which still contains excess 2,4-dihalogeno-5-nitrothiazole of the formula (II), itself is freely soluble in petroleum ether at room temperature, the 2,4-dihalogeno-5-nitrothiazole of the formula (II) is subjected to fractional sublimation or distillation, for example in vacuo at about 0.1 mbar, to separate it from the reaction product which, in most cases, is markedly less volatile. In the case of 2,4-dichloro-5-nitrothiazole, this is possible at a temperature of, for example, about 70° C and at 0.1 mbar. The reaction products can be further purified for example by recrystallization, by sublimation or by means of chromatography.

In the event that a reaction product is obtained as an oil when stirred in excess ice-water, it is isolated by repeated extraction by shaking with one of the customary organic solvents which are not miscible with water, such as, for example, methylene chloride, by a process in which the organic phase is separated off and, if appropriate, washed with water, for example in the case of dimethylformamide or N-methyl-2-pyrrolidinone as the reaction medium, followed by drying and concentration in vacuo.

The 2-amino-4-halogeno-5-nitrothiazole derivatives of the formula (IV) which are required as starting substances in process (b) according to the invention are the subject-matter of German Application P 38 24 520.5, supra.

They are obtained by reacting 2,4-dihalogeno-5-nitrothiazoles of the formula (II) with nucleophiles of the formula (X)

$$H_2N-R \quad (X)$$

in which

R is as defined above, if appropriate in the presence of acid-binding agents and in the presence of diluents. Preparatory details of these reactions can be seen from the preparation examples.

The halogenocarbonyl compounds of the formula (V) which are furthermore required as starting substances in process (b) according to the invention are basically known. In the event that specific compounds have not yet been described, they can be prepared by known methods.

4-Chlorocarbonyl-2,5-dichlorothiazole, which is used as starting material for compound No. 19, is the subject-matter of the German Patent Appl. P 38 21 598.5 of June 27, 1988, corresponding to U.S. Appl. S.N. 366,580, filed June 15, 1989, now pending. Starting from 2-chloro4-methythiazole, which is known from the literature (J.Chem.Soc. 1919, 1071-1090), . it is prepared as shown in the following equation:

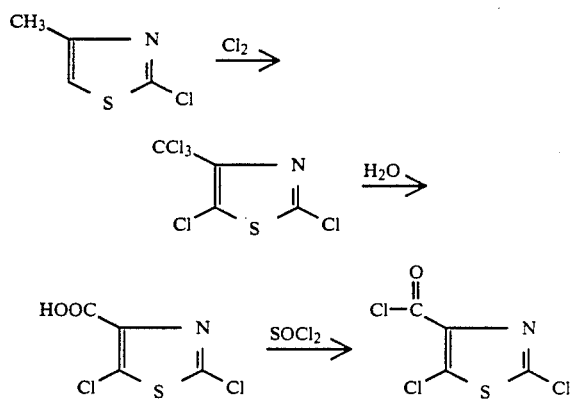

Preparatory details of these reactions can be seen from the preparation examples.

Suitable solvents for carrying out process (b) according to the invention are: aliphatic or aromatic nitriles, for example acetonitrile, propionitrile, benzonitrile, in particular acetonitrile, ethers, in particular cyclic ethers such as dioxane and tetrahydrofuran, in particular dioxane.

The reaction temperature in process (b) according to the invention can be varied over a wide range. In general the process is carried, out at between −20° C. and +150° C., preferably at 0° C. to 100° C.

As a rule, the reactions are carried out under atmospheric pressure, but they can also be carried out in closed vessels in which an accordingly higher pressure is then established depending on the nature of the solvent and on the temperature.

An acid-binding agent is not required in all cases for binding the hydrogen halide which is liberated in process (b) according to the invention, as shown in the equation. If the process is carried out without acid-binding agent, the reaction temperature chosen is expediently the reflux temperature of the particular solvent. If acid-binding agents are used, the following are suitable for this purpose: alkali metal hydroxides, alkali metal carbonates, alkali metal hydrogen carbonates or alkali metal hydrides, for example sodium hydride. In these cases, room temperature is particularly suitable as the reaction temperature.

In general, the reactants are reacted with each other in the stoichiometrically equimolar ratio, but it is also possible to employ an excess of halogenocarbonyl compound of the formula (V), which can be up to 100 %.

When carrying out process (b) according to the invention, the 2-amino-4-halogeno-5-nitrothiazole derivative of the formula (IV) is preferably dissolved in one of the mentioned solvents, the preferably equimolar to 1.5-molar amount of halogenocarbonyl compound of the formula (V) is added and, if appropriate, the equimolar to 1.5-molar amount of one of the mentioned acid-binding agents is added, and the ,mixture is stirred at the desired reaction temperature until the reaction is complete. The course of the reaction can easily be monitored by means of thin-layer chromatography. Depending on the reactants and reaction conditions, the reaction times are between one and one hundred hours.

The carboxylic anhydrides of the formula (VI) additionally required as starting substances in process (c) according to the invention are basically known. In the event that specific compounds have not been described yet, they can be prepared by known processes.

Suitable solvents for carrying out process (c) according to the invention are: aliphatic or aromatic nitriles, for example acetonitrile, propionitrile or benzonitrile, in particular acetonitrile, and ethers, in particular cyclic ethers, such as dioxane or tetrahydrofuran, in particular dioxane.

The reaction temperature in process (c) according to the invention can be varied in wide ranges. In general, the process is carried out at between 50° C. and 200° C., preferably at 60° C to 150° C.

As a rule, the reactions are carried out under atmospheric pressure, but they can also be carried out in closed vessels in which then an accordingly higher pressure is established depending on the nature of the solvent and on the temperature.

The starting substances which are preferably employed in process (c) according to the invention are aliphatic carboxylic anhydrides. In these cases, it is particularly preferred to employ an excess of aliphatic carboxylic anhydride instead, of one of the mentioned solvents. In general, 5 to 20 ml of aliphatic carboxylic anhydride are then employed per gram of starting compound (IV) to be acylated, and the mixture is refluxed until the reaction is complete. Depending on the reactants and the reaction conditions, the reaction times are between one and one hundred hours.

If R in formula (IV) is an aryl radical, in particular a phenyl radical, and if this is substituted by hydroxyl groups or amino groups, these groups are also acylated in the reaction in an excess of aliphatic carboxylic anhydride, in particular in acetic anhydride. Preparative details of these reactions can be seen from the preparation examples.

If the process is carried out using an excess of aliphatic carboxylic anhydride, working-up is particularly easy. The mixture is evaporated to dryness in vacuo, for example in a rotavapor. To remove the last residual carboxylic anhydride, the batch is either dried to constant weight between earthenware plates, or it is stirred in water, filtered off and dried.

The isocyanates of the formula (VII) required as starting substances in process (d) according to the invention are basically known. In the event that specific compounds have not been described yet, they can be prepared by known processes.

Suitable solvents for carrying out process (d) according to the invention are: aliphatic or aromatic nitriles, for example acetonitrile, propionitrile or benzonitrile, in particular acetonitrile, and ethers, in particular cyclic ethers, such as dioxane or tetrahydrofuran, in particular dioxane.

The reaction temperature in process (d) according to the invention can be varied in wide ranges. In general, the process is carried out at between 50° C. and 200° C., preferably at 60° C. to 150° C.

As a rule, the reactions are carried out under atmospheric pressure, but they can also be carried out in closed vessels in which then an accordingly higher pressure is established depending on the nature of the solvent and on the temperature.

In general, the reactants are reacted with each other in the stoichiometrically equimolar ratio. However, it is possible to employ an excess of isocyanate of the formula (VII) which can be up to 50 mole %.

For carrying out process (d) according to the invention, the 2-amino-4-halogeno-5-nitrothiazole derivative of the formula (IV) is dissolved in one of the mentioned solvents, the isocyanate of the formula (VII) is added, and the mixture is heated at the desired temperature, preferably at the reflux temperature which is established in the specific solvent, until the reaction is complete. Depending on the reactants and reaction condition, the reaction times are generally between one and one hundred hours.

The 4-halogeno-2-halogenocarbonylamino-5-nitrothiazole derivatives of the formula (VIII) required as starting substances in process (e) according to the invention are new and likewise part of the invention. They are obtained by reacting 2-amino-4-halogeno-5-nitrothiazole derivatives of, the formula (IV), where R is as defined above, with the exception that R is not hydrogen, with carbonyl dihalides of the formula (XI)

$$O=C(Hal^4)_2 \qquad (XI)$$

where $Hal^4$ is as defined above, in a solvent which is inert towards the reactants.

If 2-methylamino-4-chloro-5-nitrothiazole and phosgene are used as starting substances, the course of the process can be represented by the following equation:

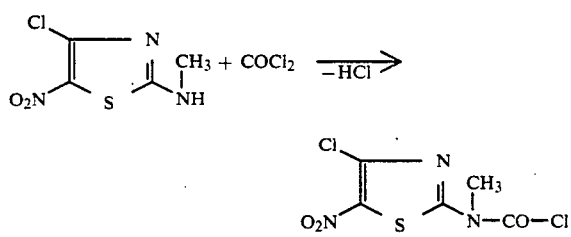

Suitable solvents for carrying out the process for the preparation of the precursors of the formula (VIII) are: hydrocarbons, such as benzene, methylbenzenes, halogenobenzenes, furthermore ethers, in particular cyclic ethers, in particular dioxane.

The reaction temperature in the process for the precursors of the formula (VIII) can be varied within wide ranges. In general, the reaction is carried out at between 0° C. and 200° C., preferably at 50° C. to 150° C.

As a rule, the reactions are carried out under atmospheric pressure, but they can also be carried out in closed vessels in which then a correspondingly higher pressure is established, depending on the nature of the solvent and on the temperature.

In carrying out the process for the preparation of the precursors of the formula (VIII), one of the mentioned solvents is added to the 2-amino-4-halogeno-5-nitrothiazole derivative of the formula (IV), and the mixture is treated preferably with phosgene, preferably at the reflux temperature of the solvent with at least the stoichiometrically required amount of the carbonyl dihalide of the formula (XI), preferably by passing the carbonyl dihalide through the reaction mixture, until the reaction to give (VIII) is complete. The course of the reaction can easily be monitored by thin-layer chromatography. The reaction times are between one and one hundred hours.

An acid-binding agent is not required in all cases to bind the hydrogen halide which is liberated in the process for the preparation of the precursors of the formula (VIII) according to the equation. If acid-binding agents are used, the following are suitable for this purpose: alkali metal hydroxides, alkali metal carbonates, alkali metal hydrogen carbonates or alkali metal hydrides, for example sodium hydride.

The nucleophiles of the formula (IX) furthermore required as starting substances in process (e) according to the invention are basically known. If specific compounds have not been described yet, they can be prepared by known processes.

Suitable solvents for carrying out process (e) according to the invention ,are: aliphatic or aromatic nitriles, for example acetonitrile, propionitrile or benzonitrile, in particular acetonitrile, and ethers, in particular cyclic ethers, such as dioxane or tetrahydrofuran, in particular dioxane.

The reaction temperature in process (e) according to the invention can be varied in wide ranges. In general, the reaction is carried out at between $-20°$ C. and $+150°$ C., preferably at $0°$ C. to $100°$ C.

The reactions are generally carried out under atmospheric pressure, but they can also be carried out in closed vessels in which then a correspondingly higher pressure is established, depending on the nature of the solvent and on the temperature.

The reactants in process (e) are preferably reacted with each other in the stoichiometrically equimolar ratio. In the case of lower aliphatic alcohols as nucleophiles of the formula (IX), these are preferably simultaneously employed as the solvent. In general, 5 to 100 ml of the aliphatic alcohol are then employed per gram of compound of the formula (VIII).

An acid-binding agent is not required in all cases for binding the hydrogen halide which is liberated in process (e) according to the invention, according to the equation, for example not in the case of aliphatic alcohols. If acid-binding agents are used, the following are suitable for this purpose, inter alia: organic tertiary amines, for example triethylamine or pyridine. If primary or secondary amines which act as bases are used as the nucleophile of the formula (IX), these can be used as acid-binding agents by employing twice the stoichiometrical amount. Furthermore, inorganic acid-binding agents can be used. The following are suitable for this purpose: alkali metal hydroxides, alkali metal carbonates, alkali metal hydrogen carbonates or alkali metal hydrides, for example sodium hydride.

In carrying our process (e) according to the invention, the 4-halogeno-2-halogenocarbonylamino-5-nitrothiazole derivative of the formula (VIII) is dissolved in one of the mentioned solvents, and the nucleophile of the formula (IX) is then added. If required, the acid-binding agent is then added, and the mixture is kept in the indicated temperature range until the reaction is complete. The reaction times are between one minute and ten hours, depending on the reactants and the reaction conditions.

The active compounds of the formula (I) according to the invention have a powerful action against pests and can employed in practice for combating undesired harmful organisms. The active compounds are suitable for use as plant protection agents, inter alia as fungicides, and furthermore also for use for the protection of industrial materials against microbes, such as, for example, fungi.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

Some causative organisms of fungal and bacterial diseases which come under the generic names listed above may be mentioned as examples, but not by way of limitation:

Xanthomonas species, such as, for example, *Xanthomonas* campestris pv. oryzae;

Pseudomonas species, such as, for example, *Pseudomonas syringae* pv. lachrymans;

Erwinia species, such as, for example, *Erwinia amylovora*; Pythium species, such as, for example, *Pythium* ultimum; Phytophthora species, such as, for example, *Phytophthora infestans;*

Pseudoperonospora species, such as, for example, *Pseudoperonospora humuli* or *Pseudoperonospora cubense;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P.* graminea (conidia form: Drechslera, syn: Helminthosporium);

Cochliobolus species, such as, for example, *Cochliobolus sativus* (conidia form: *Drechslera,* syn: Helminthosporium);

Uromyces species, such as, for example, *Uromyces appendiculatus;*

Puccinia species, such as, for example, *Puccinia recondita;*

Tilletia species, such as, for example, *Tilletia* caries; Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;* Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae* and

Pseudocercosporella species, such as, for example, *Pseudocercosporella herpotrichoides.*

In this context, the active compounds according to the invention can be employed with particularly good success for combating diseases of fruit, vegetables and cereals, such as, for example, against the pathogen causing apple scab (*Venturia inaequalis*), against the pathogen causing tomato blight (*Phytophthora infestans*), against pathogens causing vine diseases (*Plasmopara viticola*), or against pathogens causing cereal diseases, such as, for example, *Leptosphaeria nodorum, Cochliobolus sativus* and *Pyrenophora teres*. The action against pathogens causing rice diseases (*Pyricularia oryzae*) and the good in-vitro action may also be mentioned.

The good toleration by plants of the active compounds, at the concentrations required for combating plant diseases, permits treatment of aerial parts of plants, of vegetative propagation stock and seeds, and of the soil.

The active compounds can be converted into the customary formulations, such as solutions, emulsions, suspensions, powders, foams, pastes, granules, aerosols, very fine capsules in polymeric substances and in coating compositions for seeds, as well as ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at ambient temperature and under atmospheric pressure, for example aerosol propellants, such as halogen hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as ,sawdust, coconut shells, corn cobs and tobacco stalks. As emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and other growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

Due to their broad spectrum of action, the active compounds according to the invention of the formula (I) are furthermore also suitable for the protection of industrial materials.

Since industrial materials can be attacked and damaged by a large number of very different microbe species, a broad spectrum of action, which also facilitates numerous uses, is an essential property of modern substances for the protection of materials.

According to the invention, industrial materials are non-live materials which have been prepared for use in industry. For example, industrial materials which are to be protected by active compounds according to the invention from microbial change or destruction can be glues, sizes, paper and board, textiles, leather, wood, paints and plastic articles, cooling lubricants and other materials which can be attacked and decomposed by microorganisms. Parts of production plants, for example cooling-water circuits, which may be impaired by multiplication of microorganisms may also be mentioned within the scope of the materials to be protected. Industrial materials which may be mentioned in the scope of the present invention are preferably glues, sizes, papers and boards, leather, wood, paints, cooling lubricants and cooling circuits.

Microorganisms, capable of a degradation of, or a change in, industrial materials, which may be mentioned are, for example, bacteria, fungi, yeasts, algae and slime organisms. The active compounds according to the invention preferably act against fungi, in particular moulds, wood-discolouring and wood-destroying fungi (Basidiomycetes), and against bacteriale, slime organisms and algae.

Microorganisms of the following genera may be mentioned as examples:
Alternaria, such as *Alternaria tenuis,*
Aspergillus, such as *Aspergillus niger,*
Chaetomium, such as *Chaetomium globosum,*
Coniophora, such as *Coniophora puteana,*
Lentinus, such as *Lentinus tigrinus,*
Penicillium, such as *Penicillium glaucum,*
Polyporus, such as *Polyporus versicolor,*
Aureobasidium, such as *Aureobasidium pullulans,*
Sclerophoma, such as *Sclerophoma pityophila,*
Trichoderma, such as *Trichoderma viride,*
Escherichia, such as *Escherichia coli,*
Pseudomonas, such as *Pseudomonas aeruginosa,*
Staphylococcus, such as *Staphylococcus aureus.*

Depending on the field of application, an active substance according to the invention can be converted into the customary formulations, such as solutions, emulsions, suspensions, powders, pastes and granules.

These can be prepared by a manner known per se, for example by mixing the active compounds with an extender consisting of liquid solvent and/or solid carriers, if appropriate with the use of surface-active agents, such as emulsifiers and/or dispersants, it being possible, if appropriate, for organic solvents, such as alcohols, to be used as auxiliaries in the event that water is used as the extender.

Liquid solvents for the active compounds can be, for example, water, alcohols, such as lower aliphatic alcohols, preferably ethanol or isopropanol, or benzyl alcohol, ketones, such as acetone or methyl ethyl ketone, liquid hydrocarbons, such as petroleum fractions, or halogenated hydrocarbons, such as 1,2-dichloroethane.

Microbicidal agents contain the active compounds in general in an amount of 1 to 95 %, preferably of 10 to 75 %.

The use concentrations of the active compounds according to the invention depend on the type and the occurrence of the microorganisms to be combated as well as on the composition of the material to be protected. The optimum application rate can be determined by test series. In general, the use concentrations are in the range of 0.001 to 5 % by weight, preferably of 0.05 to 1.0 % by weight, based on the material to be protected.

The active compounds according to the invention can also be present in a mixture with other known active compounds. The following active compounds may be mentioned as examples: benzyl alcohol mono(poly)-hemiformal and other formaldehyde-liberating compounds, benzimidazolyl methylcarbamate, tetramethyl thiuram disulphide, zinc salts of dialkyl dithiocarbamates, 2,4,5,6-tetrachloroisophthalonitrile, thiazolylbenzimidazole, mercaptobenzothiazole, 2-rhodanidomethylthiobenzothiazole, organo-tin compounds, methylene bisthiocyanate, phenol derivatives, such as 2-phenylphenol, (2,2,-dihydroxy-5,5,-dichloro)-diphenylmethane and 3-methyl-4-chloro-phenol and N-trihalogenomethylthio compounds.

The preparation and the use of the active compounds according to the invention can be seen from the examples which follow.

PREPARATION EXAMPLE EXAMPLE 1

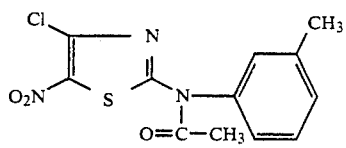

(Compound No. 42)

A mixture of 5.0 g (18.55 mmol) of 4-chloro-2-(3-methylphenylamino)-5-nitrothiazole (melting point 175° C. with decomposition; preparation analogous to Example A4) and 50 ml of acetic anhydride is refluxed for one hour, while stirring. The excess acetic anhydride and the acetic acid which has formed are subsequently distilled off in a rotary evaporator under a water pump vacuum, the residue is stirred with water at room temperature, and the solid is filtered off with suction and dried. This gives 5.5 g (95.2 % of theory) of 2-[N-acetyl-N-(3-methylphenyl)]-amino-4-chloro-5-nitrothiazole of melting point 137° C. to 138° C.

EXAMPLE 2

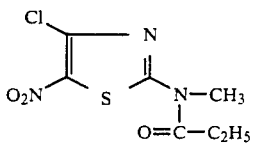

(Compound No. 4)

A mixture of 251.6 g (1.30 mol) of 4-chloro-2methylamino-5-nitrothiazole (melting point 212° C. with decomposition; preparation see Example A8) and 1000 ml of propionic anhydride is refluxed for, one hour, while stirring. At this stage, the thin-layer chromatogram (mobile phase toluene/ethyl acetate 4:1) shows that starting compound is no longer present. The stirred reaction mixture is subsequently cooled to about 8° C., and the precipitate which has formed is filtered off, washed with a little propionic anhydride and then with petroleum ether, and dried. This gives 254.3 g (78.4 % of theory) of 2-(propionyl-methylamino)-4-chloro-5-nitrothiazole of melting point 132° C. to 133,° C. Stirring the propionic anhydride mother liquor with 6 liters of water overnight at room temperature, followed by filtration of the precipitate which has formed, washing the latter with water and drying it, gives a further 49.0 g (15.1 % of theory) of 2-(propionyl-methylamino)-4-chloro-5-nitrothiazole. Total yield: 93.5 % of theory.

EXAMPLE 3

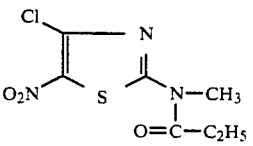

(Compound No. 4)

A mixture of 3.87 g (0.02 mol) of 4-chloro-2-methylamino-5-nitrothiazole (melting point 212° C. with decomposition; preparation see Example A8), 2.78 g (0.03 mol) of propionyl chloride and 50 ml of dioxane is refluxed for about 70 hours, while stirring. After the mixture has cooled, it is stirred with 500 ml of ice-water, and the solid is filtered off, washed with water and dried. This gives 4.60 g (92.2 % of theory) of 2-(propionyl-methylamino)-4-chloro-5-nitrothiazole, which is identical in all properties with the compound obtained according to Example 2.

EXAMPLE 4

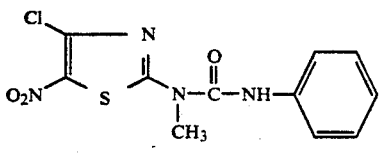

(Compound No. 70)

A mixture of 1935 mg (10 mmol) of 4-chloro-2-methylamino-5-nitrothiazole (melting point 212° C. with decomposition; preparation see Example A8), 1430 mg (12 mmol) of phenyl isocyanate and 50 ml of dioxane is refluxed for 22 hours, while stirring. The mixture is cooled to room temperature, and the precipitate which has formed is filtered off, washed with dioxane and dried. This gives 1935 mg (61.9 % of theory) of the urea derivative of the above formula of melting point 225° C. with decomposition.

EXAMPLE 5

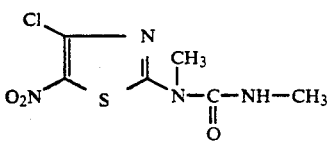

(Compound No. 2)

22.0 g (0.25 mol) of N,N'-dimethylurea are added to a solution of 60.0 g (0.302 mol) of 2,4-dichloro-5-nitrothiazole in 250 ml of N-methyl-2-pyrrolidinone, and the mixture is heated at 65° C. for about 20 hours, while stirring. It is then cooled to room temperature and stirred with 2 liters of ice-water. This results in the formation of an oily precipitate which is transformed into a pulverulent precipitate by the addition of about 200 ml of methylene chloride. It is filtered off, washed with water and dried. This gives 18.9 g (25.0 % of theory) of the urea derivative of the above formula of melting point 224° C., to 225° C. with decomposition amber-yellow crystals from a little methanol.

The identical compound is also obtained analogously to Example 4 from 4-chloro-2-methylamino-5-nitrothiazole and methyl isocyanate in boiling dioxane.

EXAMPLE 6

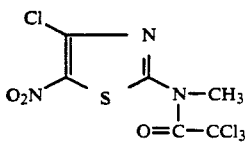

(Compound No. 15)

A mixture of 3.87 g (0.02 mol) of 4-chloro-2-methylamino-5-nitrothiazole (melting point 212° C. with decomposition; preparation see Example A8), 4.55 g (0.025 mol) of trichloroacetyl chloride and 50 ml of dioxane is refluxed for 2 hours, while stirring. After the mixture has been cooled, it is stirred with 400 ml of ice-water, and the solid is filtered off, washed with water and dried This gives 6.50 g (95.9 % of theory) of 4-chloro-2-(methyl-trichloroacetyl-amino)-5-nitrothiazole of melting point 146° C. to 149° C. with decomposition.

EXAMPLE 7

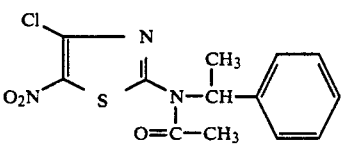

(Compound No. 101)

A mixture of 2.70 g (9.52 mmol) of 4-chloro-5-nitro-2-(1-phenethylamino)-thiazole (melting point 108° C. from cyclohexane; preparation analogously to Example A4) and 27 ml of acetic anhydride is refluxed for about 70 hours, while stirring. The mixture is worked up analogously to Example 1. This gives 1.95 g (62.9 %) of the compound of the above formula of melting point 117° C. to 118° C. with decomposition.

EXAMPLE 8

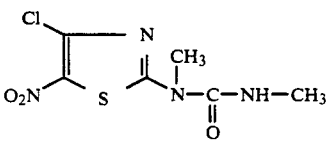

(Compound No. 2)

A mixture of 0.62 g (8 mmol) of 40 % strength aqueous methylamine and 5 ml of dioxane is added dropwise at about 15° C. to a solution of 1.02 g (4 mmol) of 4-chloro-2-(N-chlorocarbonyl-N-methyl)-amino-5-nitrothiazole (preparation see Example A9) in 10 ml of dioxane, a solid precipitating immediately. Stirring is continued for 15 minutes, and the mixture is stirred with 150 ml of ice-water, and the solid is filtered off, washed with water and dried. This gives 0.96 g (96.2 % of theory) of the urea derivative of the above formula, which is identical in all properties with the product obtained in Example 5.

EXAMPLE 9

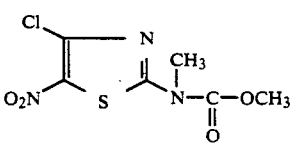

(Compound No. 104)

1.28 g (5 mmol) of 4-chloro-2-(N-chlorocarbonyl-N-methyl)-amino-5-nitrothiazole and 50 ml of methanol are heated to the boil for 10 minutes. It is then evaporated to dryness in a water pump vacuum. 1.25 g (99 % of theory) of the carbamic acid derivative of the above formula of melting point 157° C. to 158° C. remain.

An identical product is obtained when the mixture is stirred vigorously at room temperature for about one hour instead of heating it to the boil for 10 minutes.

EXAMPLE 10

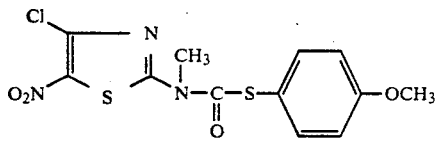

(Compound No. 105)

395 mg (3.9 mmol) of triethylamine are added at room temperature to a solution of 1000 mg (3.9 mmol) of 4-chloro-2-(N-chlorocarbonyl-N-methyl)-amino-5-nitrothiazole (preparation see Example A9) and 547 mg (3.9 mmol) of 4-mercaptoanisole in 20 ml of dioxane, a solid precipitating immediately. Stirring is continued for one hour, and the mixture is then stirred with about 200 ml of water, and the solid is filtered off, washed with water and dried. This gives 1400 mg (99.7 % of theory) of the thiocarbamic acid derivative of the above formula of melting point 183° C. to 184° C.

EXAMPLE 11

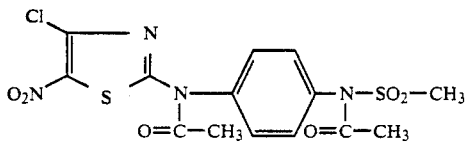

(Compund No. 85)

A mixture of 5.0 g (14.35 mmol) of 4-chloro-2-(4-methylsulphonylaminophenylamino)-5-nitrothiazole (melting point 203° C. with decomposition; preparation analogously to Example A4) and 100 ml of acetic anhydride is refluxed for about 20 hours, while stirring. The mixture is then evaporated to dryness in a water pump vacuum, and the residue is dried overnight between two earthenware plates. This gives 5.2 g (84 % of theory) of the diacetyl derivative of the above formula of melting point 246° C. to 247° C. with decomposition.

EXAMPLE 12

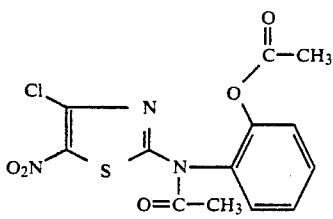

(Compound No. 6)

4-Chloro-2-(2-hydroxyphenylamino)-5-nitrothiazole (melting point 204° C.; preparation analogously to Example A4) is reacted analogously to Example 1. This gives the diacetyl derivative of the above formula of melting point 151° C., likewise in a very good yield.

EXAMPLE 13

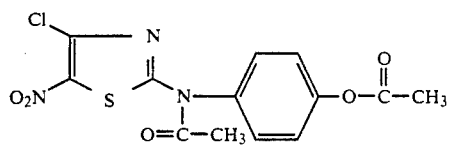

(Compound No. 62)

4-Chloro-2-(4-hydroxyphenylamino)-5-nitrothiazole (melting point 174° C. to 176° C. with decomposition; preparation analogously to Example A4) is reacted analogously to Example 1. This gives the diacetyl derivative of the above formula of melting point 197° C, likewise in a very good yield.

EXAMPLE 14

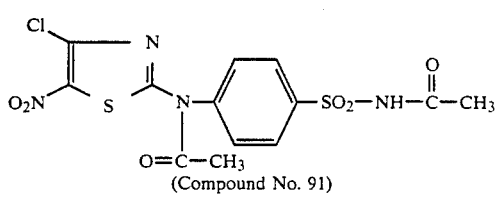

(Compound No. 91)

2-(4-Aminosulphonylphenylamino)-4-chloro-5-nitrothiazole (melting point above 280° C.; preparation analogously to Example 4) is reacted analogously to Example 1. This gives the diacetyl derivative of the above formula of melting point 244° C. with decomposition, likewise in a very good yield.

EXAMPLE 15

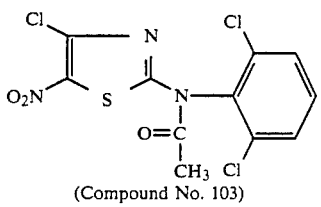

(Compound No. 103)

4-Chloro-2-(2,6-dichlorophenylamino)-5-nitrothiazole (melting point 141° C.; preparation see Example A10) is reacted analogously to the instructions of Example 1, with the difference that it is refluxed for 40 hours instead of one hour. Thin-layer chromatography analysis shows that starting product is then no longer present. Working-up analogously to Example 1 gives 2-(N-acetyl-N-2,6-dichlorophenyl)-amino-4-chloro-5-nitrothiazole of melting point 95° C., likewise in a very good yield.

EXAMPLE 16

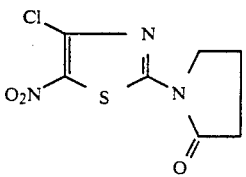

(Compound No. 107)

1.8 g (0.06 mol) of sodium hydride (80 % of substance in paraffin) are added in portions at about 0–5° C. to a stirred solution of 19.9 g (0.1 mol) of 2,4-dichloro-5-nitrothiazole and 4.25 g (0.05 of pyrorolidin-(2)-one in 150 ml of tetrahydrofuran. Stirring is continued for 4 hours at room temperature, and the mixture is then stirred into 1 1 of ice-water and acidified using hydrochloric acid. The supernatant is decanted off from the semi-solid precipitate, and the latter is stirred vigorously with 500 ml of petroleum ether. After this, the precipitate which is now pulverulent is filtered off, rinsed with petroleum ether and dried. The crude product (9.42 g) is purified by sublimation at 150° C./0.1 mbar. This gives 2.05 g (16.6 % of theory) of the pyrrolidinone derivative of the above formula of melting point 172.5° C. to 173° C. (from cyclohexane).

EXAMPLE 17

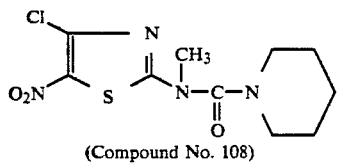

(Compound No. 108)

0.85 g (0.01 mol) of piperidine is added at room temperature to a stirred solution of 1.28 g (0.005 mol) of 4-chloro-2-(N-chlorocarbonyl-N-methyl)-amino-5-nitrothiazole in 200 ml of dioxane, a solid precipitating immediately. Stirring is continued for 15 minutes, and the mixture is then stirred into 200 ml of water, and the solid is filtered off, washed with water and dried. This gives 1.48 g (97.4 % of theory) of the urea of the above formula. The melting point is 168° C. to 171° C., after recrystallization from cyclohexane.

EXAMPLE 18

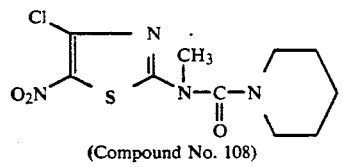

(Compound No. 108)

960 mg (6.51 mmol) of N-chlorocarbonylpiperidine and 899 mg (6.51 mmol) of potassium carbonate are added to a solution of 840 mg (4.34 mmol) of 4-chloro-2-methylamino- 5-nitrothiazole in 200 ml of acetonitrile. The mixture is stirred overnight at room temperature, then stirred with 1 1 of water and acidified using hydrochloric acid, and the solid is filtered off, washed with water and dried. This gives 850 mg (64.3 % of theory) of the urea of the above formula, which is identical with the product obtained in Example 17. Instead of by recrystallization from cyclohexane, the compound can also be purified by sublimation at 130° C./0.1 mbar.

Preparation of starting materials hitherto unknown from the literature

EXAMPLE A1

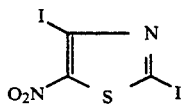

19.9 g (0.1 mol) of 2,4-dichloro-5-nitrothiazole are dissolved in 500 ml of acetone, 150 g (1 mol) of sodium iodide are added, and the mixture is then refluxed for about 60 hours. According to analysis by gas chromatography, the proportion of 2,4-diiodo-5-nitrothiazole in the reaction mixture is then more than 95 %. In the next step, the solvent is stripped off in vacuo, and the residue is stirred in water, filtered off, washed with water and dried. Recrystallization from cyclohexane gives 33.9 g (89 % of theory) of 2,4-diiodo-5-nitrothiazole of melting point 135° C.

EXAMPLE A2

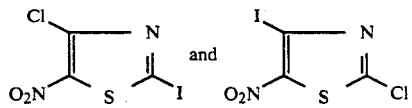

39.8 g (0.2 mol) of 2,4-dichloro-5-nitrothiazole are dissolved in 500 ml of acetone, 90 g (0.6 mol) of sodium iodide are added, and the mixture is then stirred at room temperature for about 6 days, during which process the procedure of the reaction is monitored by gas chromatography. The solvent is then stripped off in vacuo, and the residue is stirred in water, filtered off, washed with water and dried. This gives a substance mixture which, according to analysis by gas chromatography, contains 71.5 % of 2-iodo-4-chloro-5-nitrothiazole and 25.8 % of 2-chloro-4-iodo-5-nitrothiazole. Separation by HPLC-chromatography (=high-pressure liquid chromatography) yields the pure substances of the following melting points: 2-iodo-4-chloro-5-nitrothiazole: melting point 80° C.–81° C., 2-chloro-4-iodo-5-nitrothiazole: melting point 108° C.–109.5° C.

EXAMPLE A3

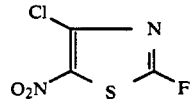

19.9 g (0.1 mol) of 2,4-dichloro-5-nitrothiazole are dissolved in 60 ml of acetonitrile, 24 g (0.4 mol) of calcined potassium fluoride and 0.5 g of [18]crown-6 are added, and the mixture is then stirred at room temperature for about one week, during which process the procedure of the reaction is monitored by gas chromatography. The crude batch is distilled at 0.1 to 0.2 mbar and at a temperature of 20° to 25° C., during which process the volatile constituents are collected in a receiver cooled with methanol/dry ice. The acetonitrile is subsequently distilled off under atmospheric pressure, a mixture of approximately equal parts of 4-chloro-2-fluoro-5-nitrothiazole and 2,4-dichloro-5-nitrothiazole remaining. 4-Chloro-2-fluoro-5-nitrothiazole can be separated from this mixture for example by fractional distillation.

$^{19}$F—NMR (CDCl$_3$) (CF$_3$—COOH as the external standard): δ = −17.5 ppm.

MS: 182 (37%) = M$^+$ = C$_3$ClFN$_2$O$_2$S
124 (34%)
91 (60%)
63 (100%)

By gas chromatography, the isomeric 2-chloro-4-fluoro-5-nitrothiazole can be identified as a secondary component in a relative proportion of between 1 and 5 % based on 4-chloro-2-fluoro-5-nitrothiazole.

$^{19}$F—NMR (CDCl$_3$) (CF$_3$—COOH as the external standard): δ = −22.7 ppm.

MS: 182 (83%) = M = C$_3$ClFN$_2$O$_2$S
136 (32%)
91 (43%)
75 (100%)

EXAMPLE A4

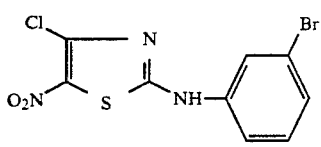

A solution of 8.6 g (0.05 mol) of 3-bromoaniline in 100 ml of dimethylformamide is added dropwise at 0° C. to 5° C. in the course of about 2 hours to a solution of 12.0 g (0.06 mol) of 2,4-dichloro-5-nitrothiazole in 100 ml of dimethylformamide, and stirring is continued for 4 hours at the same temperature. The mixture is then stirred into 1000 ml of ice-water, and the precipitate is filtered off, washed with water and dried. To remove excess 2,4-dichloro-5-nitrothiazole, the product is stirred into 80 ml of petroleum ether at room temperature, and the solid is filtered off, washed with petroleum ether and dried. This gives 16.0 g (95.7 % of theory) of 2-(3-bromophenylamino)-4-chloro-5-nitrothiazole of melting point 191° C. to 192° C. (decomposition)

EXAMPLE A5

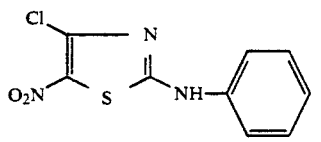

252 g (3.0 mol) of sodium hydrogen carbonate are added to a solution of 360 g (1.8 mol) of 2,4-dichloro-5-nitrothiazole in 1.5 l of acetonitrile. A mixture of 139.5 g (1.5 mol) of aniline and 1500 ml of acetonitrile is subsequently added dropwise at −10° C. to −15° C. in the course of about 4.5 hours, and stirring is continued at the same temperature for another 4 hours. The mixture is then stirred into 15 l of ice-water, and, the precipitate is filtered off, washed with water and dried. To remove excess 2,4-dichloro-5-nitrothiazole, the product is stirred into 2.4 l of petroleum ether at room temperature, and the solid is filtered off, washed with petroleum ether and dried. This gives 361.7 g (94.4 % of theory) of 2-anilino-4-chloro-5-nitrothiazole of melting point 186° C. to 187° C. (decomposition).

EXAMPLE A6

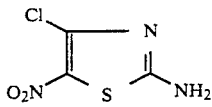

10.1 g (0.105 mol) of ammonium carbonate are added to a stirred solution of 19.9 g (0.1 mol) of 2,4-dichloro-5-nitrothiazole in 200 ml of acetonitrile, and stirring is continued for two days at room temperature. The mixture is subsequently stirred into 1 l of icewater, and the precipitate is filtered off, washed with water and dried. To remove unreacted 2,4-dichloro-5-nitrothiazole, the product is stirred into about 100 ml of petroleum ether at room temperature, and the solid is filtered off, washed with petroleum ether and dried. This gives 12.2 g (68.0 % of theory) of 2-amino-4-chloro-5-nitrothiazole of melting point 180° C. (decomposition).

EXAMPLE A7

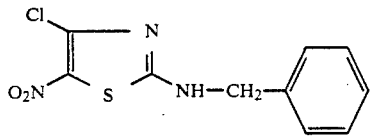

7.0 g (0.051 mol) of anhydrous potassium carbonate are added to a solution of 12.0 g (0.06 mol) of 2,4-dichloro-5-nitrothiazole in 50 ml of acetonitrile. A mixture of 5.35 g (0.05 mol) of benzylamine and 50 ml of acetonitrile is subsequently added dropwise at 15° C. to 20° C. in the course of about half an hour, and stirring is continued for one further hour at room temperature. The mixture is subsequently refluxed for 15 minutes, cooled to room temperature and stirred into about 500 ml of ice-water, and the precipitate is filtered off, washed with water and dried. To remove excess 2,4-dichloro-5-nitrothiazole, the product is stirred into 80 ml of petroleum ether at room temperature, and the solid is filtered off, washed with petroleum ether and dried. This gives 12.9 g (95.7 % of theory) of 2-benzylamino-4-chloro-5-nitrothiazole of melting point 195° C. to 196° C. (decomposition).

EXAMPLE A8

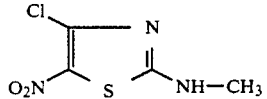

315.3 g (3.0 mol) of 29.5 % strength aqueous methylamine solution are slowly added dropwise at −10° C. to 0° C. to a solution of 398 g (2.0 mol) of 2,4-dichloro-5-nitrothiazole in 2500 ml of acetonitrile. Stirring is continued overnight at room temperature, the mixture is then stirred into 15 liters of ice-water, and the precipitate is filtered off, washed with water and dried. The solid is stirred with about 1.5 liters of petroleum ether and then filtered off at room temperature, washed with petroleum ether and dried. This gives 289.0 g (74.7 % of theory) of 4-chloro-2-methylamino-5-nitrothiazole of melting point 212° C. (decomposition). The compound can be recrystallized from methanol, and sublimation may be carried out at 140° C./0.1 mbar.

EXAMPLE A9

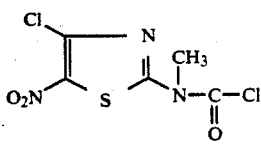

A vigorous stream of phosgene is passed into a boiling suspension of 19.4 g (0.1 mol) of 4-chloro-2-methylamino-5-nitrothiazole in 350 ml of dioxane (90°-95° C.). After about 15 minutes, a clear solution is obtained. Phosgene is passed in for about two more hours and then displaced using dry nitrogen, and the mixture is concentrated in a water pump vacuum at a bath temperature of 40° C. 25.4 g (99 % of theory) of 4-chloro-2-(N-chlorocarbonyl-N-methyl)-amino-5-nitrothiazole remain. Melting point after recrystallization from cyclohexane: 130° C. to 131° C.

EXAMPLE A10 a)
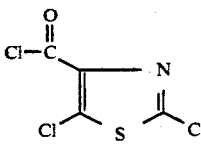
(Starting material for compound No. 19)

A stirred mixture of 143.5 g (0.725 mol) of 2,5-dichlorothiazole-4-carboxylic acid and 700 ml of thionyl chloride is slowly heated. Vigorous evolution of gas starts already at about 40° C. The mixture is brought to reflux temperature in the course of half an hour and maintained at this temperature until evolution of gas has ceased (about 2 hours): end temperature about 80° C.

After the excess thionyl chloride has been stripped off in a water pump vacuum, 144.6 g (92.2 % of theory) of crystalline 4-chlorocarbonyl-2,5-dichlorothiazole remain, large, colorless crystals of melting point 58°-59° C. from petroleum ether.

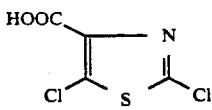

271.5 g (1 mol) of 2,5-dichloro-4-trichloromethyl-thiazole and 2700 ml of water are refluxed overnight (about 15 hours), while stirring. After the mixture has been cooled to room temperature, the crystalline precipitate which has formed is filtered off, washed with water and dried. Yield 143.5 g (72.5 % of theory) of 2,5-dichlorothiazole-4-carboxylic acid. The compound may be subjected to sublimation at 120° C/0.1 mbar, and can be recrystallized for example from chloroform, melting point 191° C. with decomposition. By concentrating the aqueous phase, a further 30.5 g of slightly less pure product can be isolated.

c)
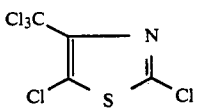

Starting from room temperature, gaseous chlorine is passed into a mixture of 1093 g (8.19 mol) of 2-chloro-4-methylthiazole and 4 l of methylene chloride in a three-necked flask equipped with stirrer, thermometer, reflux condenser and gas inlet tube. After the exothermal reaction has subsided, the methylene chloride is distilled off in a first step, while gradually increasing the temperature and more chlorine being passed in, and the bottom is then slowly heated up to about 160° C. At about 160° C., mostly excess gaseous chlorine is then passed in (recognizable from the pale greenish color of the waste gas) until the gas chromatogram shows virtually only the desired compound 2,5-dichloro-4-trichloromethyl-thiazole. Total duration of the chlorination is 40 to 50 hours.

Coarse distillation up to a head temperature of 150° C. at 14 mbar yields 2057 g of about 95 % pure 2,5-dichloro-4-trichloromethyl-thiazole, which corresponds to a yield of 88 % of theory based on the pure product. The pure 2,5-dichloro-4-trichloromethyl-thiazole is obtained by fine distillation on a packed silver-coated column about 220 cm in length Boiling point 123° C. to 125° C. at 16 mbar.

EXAMPLE A11

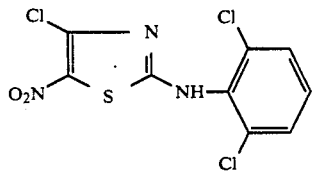

A mixture of 6.48 g (0.04 mol) of 2,6-dichloroaniline, 1.4 g (0.047 mol) of sodium hydride (80 % pure in paraffin) and 50 ml of tetrahydrofuran is stirred for 2 hours at room temperature. The suspension is subsequently added dropwise in the course of one hour to a solution of 15.92 g (0.08 mol) of 2,4-dichloro-5-nitrothiazole in 100 ml of tetrahydrofuran. Stirring is continued at room temperature for about three hours, and the mixture is then transferred into 600 ml of water, the crude product is extracted using methylene chloride, and the methylene chloride phase is dried and concentrated. The residue is subjected to sublimation at 135° C./0.1 mbar, and the sublimate is recrystallized from petroleum ether. This gives 1.2 g (9.2 % of theory) of 4-chloro-2-(2,6-dichlorophenylamino)-5-nitrothiazole of melting point 141° C.

The following 2-acylamino-4-halogeno-5-nitrothiazole derivatives of the general formula (I) are obtained in a corresponding manner and following the general preparation instructions.

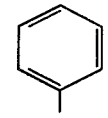

(I)

| Compound No. | Hal | End products -R | -(A)$_x$-R$^1$ | M.p. (°C.) (recryst. from) | Preparation | Starting compound M.p. (°C.) | Preparation |
|---|---|---|---|---|---|---|---|
| 1 | Cl | 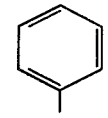 | -CH$_3$ | 176-7 | analogously to Example 1 | 186-7 (decomp.) | see Example A5 |
| 2 | Cl | -CH$_3$ | -NH-CH$_3$ | 224-5 (decomp.) | see Example 5 and see Example 8 | 212 (decomp.) 130-1 | see Ex. A8 see Ex. A9 |
| 3 | Cl | -CH$_3$ | -CH$_3$ | 178-9 | analogously to Example 2 | 212 (decomp.) | see Example A8 |
| 4 | Cl | -CH$_3$ | -C$_2$H$_5$ | 132-3 | see Example 2 and 3 | 212 (decomp.) | see Example A8 |
| 5 | Cl | 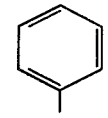 | -C$_2$H$_5$ | 151-4 | analogously to Example 1 | 186-7 (decomp.) | see Example A5 |
| 6 | Cl | 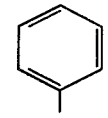 | -CH$_3$ | 151 | see Example 12 | 204 | analogously to Example A4 |
| 7 | Cl | H | -CH$_3$ | 198-202 | analogously to Example 2 | 180 (decomp.) | see Example A6 |
| 8 | Cl | 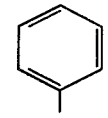 -CH$_2$- | -CH$_3$ | 174 5 (decomp.) | analogously to Example 1 | 195-6 (decomp.) | see Example A7 |

-continued $$\underset{O_2N}{\overset{Hal}{\diagdown}}C=C\underset{S}{\overset{R}{\diagdown}}N-\underset{\underset{O}{\|}}{C}-(A)_x-R^1 \quad (I)$$

| Compound No. | End products -R | Hal | -(A)x-R1 | M.p. (°C.) (recryst. from) | Preparation | Starting compound M.p. (°C.) | Preparation |
|---|---|---|---|---|---|---|---|
| 9 | 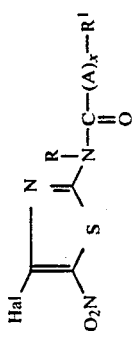 | Cl | —CH₃ | 227 (decomp.) | analogously to Example 1 | 215-6 (decomp.) | analogously to Example A4 |
| 10 | 4-F-C₆H₄ | Cl | —CH₃ | 204 (decomp.) | analogously to Example 1 | 112-3 (decomp.) | analogously to Example A4 |
| 11 | 3-SCF₃-C₆H₄ | Cl | —CH₃ | 147-8 (decomp.) | analogously to Example 1 | 77-8 | analogously to Example A4 |
| 12 | C₆H₅ | Cl | —CH₂Cl | 152-4 (decomp.) | analogously to Example 3 | 186-7 (decomp.) | see Example A5 |
| 13 | —CH₃ | Cl | —CH₂Cl | 190-190.5 | analogously to Example 3 | 212 (decomp.) | see Example A8 |
| 14 | —CH₃ | Cl | C₆H₅ | 168 | see Example 6 | 212 (decomp.) | see Example A8 |
| 15 | —CH₃ | Cl | —CCl₃ | 146-9 (decomp.) | see Example 6 | 212 (decomp.) | see Example A8 |

-continued $$\begin{array}{c} Hal \\ \diagdown \\ O_2N \end{array} C=C \begin{array}{c} N \\ \diagup \\ S \end{array} \begin{array}{c} R \\ | \\ N-C-(A)_x-R^1 \\ \| \\ O \end{array} \quad (I)$$

| Compound No. | Hal | End products R | $-(A)_x-R^1$ | M.p. (°C.) (recryst. from) | Preparation | Starting compound M.p. (°C.) | Preparation |
|---|---|---|---|---|---|---|---|
| 16 | Cl |  | —CHCl$_2$ | 167–9 (cyclohexane) | analogously to Example 3 | 186–7 (decomp.) | see Example A5 |
| 17 | Cl | —CH$_3$ | —CHCl$_2$ | 196–196.5 | analogously to Example 6 | 212 (decomp.) | see Example A8 |
| 18 | Cl | —CH$_3$ |  | 197 | analogously to Example 3 | 212 (decomp.) | see Example A8 |
| 19 | Cl | —CH$_3$ |  | 183–4 (decomp.) | analogously to Example 3 | 212 (decomp.) | see Example A8 |
| 20 | Cl | H | —CH$_2$Cl | 158–64 (decomp.) (toluene) | analogously to Example 3 | 180 (decomp.) | see Example A6 |
| 21 | Cl | H | —CHCl$_2$ | 138–40 | analogously to Example 6 | 180 (decomp.) | see Example A6 |
| 22 | Cl | H | —CCl$_3$ | 112–4 | analogously to Example 6 | 180 (decomp.) | see Example A6 |
| 23 | Cl | —CH$_3$ | 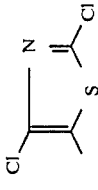 | 153–5 (decomp.) (toluene) | analogously to Example 4 | 212 (decomp.) | see Example A8 |
| 24 | Cl | —CH$_3$ | —CF$_3$ | 127–9 | analogously to Example 2 | 212 (decomp.) | see Example A8 |
| 25 | Cl | H | —CF$_3$ | 155–6 (decomp.) | analogously to Example 2 | 180 (decomp.) | see Example A6 |
| 26 | Cl |  | —CCl$_3$ | 104 (decomp.) | analogously to Example 3 | 186–7 (decomp.) | see Example A5 |

-continued $$\begin{array}{c}\text{Hal}\\\diagup\\\text{N}\\\diagup\phantom{xx}\diagdown\\\phantom{xx}\text{R}\\\phantom{xxxx}|\phantom{xxx}\text{O}\\\phantom{xxxx}\text{N}-\text{C}-(A)_x-R^1\\\diagup\phantom{xx}\diagdown\phantom{xx}\|\\\text{S}\phantom{xxxxxx}\text{O}\\\diagup\\\text{O}_2\text{N}\end{array}\quad(I)$$

| Compound No. | Hal | End products -R | -(A)ₓ-R¹ | M.p. (°C.) (recryst. from) | Preparation | Starting compound M.p. (°C.) | Preparation |
|---|---|---|---|---|---|---|---|
| 27 | Cl | -CH₃ | -CH₂-C₂H₅ | 114-5 | analogously to Example 3 | 212 (decomp.) | see Example A8 |
| 28 | Cl | -CH₃ | -CH₂-CH(CH₃)CH₃ | 94-6 | analogously to Example 3 | 212 (decomp.) | see Example A8 |
| 29 | Cl | -C₂H₅ | -CH₂Cl | 139-42 | analogously to Example 3 | 167-8 (decomp.) | analogously to Example A8 |
| 30 | Cl | -CH₂-C₂H₅ | -CH₂Cl | 117-21 | analogously to Example 3 | from 106 (decomp.) | analogously to Example A8 |
| 31 | Cl | -CH₂-CH₂-OCH₃ | -CH₂Cl | 156-9 | analogously to Example 3 | 124-8 | analogously to Example A8 |
| 32 | Cl | H | cyclohexyl (1-methyl) | 152-4 | analogously to Example 3 | 180 (decomp.) | see Example A6 |
| 33 | Cl | -CH₂-CH₂Cl | -CH₂Cl | 111.5-115 | analogously to Example 3 | 143-4 (decomp.) | analogously to Example A8 |
| 34 | Cl | -C₂H₅ | -C₂H₅ | 119.5-121 | analogously to Example 3 | 167-8 (decomp.) | analogously to Example A8 |
| 35 | Cl | -CH₂-C₂H₅ | -C₂H₅ | 99.5-100.5 | analogously to Example 3 | 167-8 (decomp.) | analogously to Example A8 |
| 36 | Cl | -CH₂-CH₂-OCH₃ | -C₂H₅ | 101.5-103 | analogously to Example 3 | 124-8 | analogously to Example A8 |
| 37 | Cl | 4-chlorophenyl | -CH₃ | 187 | analogously to Example 1 | 207 (decomp.) | analogously to Example A4 |

-continued $$\underset{O_2N}{\overset{Hal}{\vphantom{X}}}\!\!\!\!\!\!\!\!\!\!\!\!\!\!\!\!\!\!\underset{S}{\overset{N}{\|}}\!\!-\!\!\underset{R}{N}\!\!-\!\!\underset{\overset{\|}{O}}{C}\!\!-\!\!(A)_x\!\!-\!\!R^1 \qquad (I)$$

| Compound No. | Hal | End products −R | −(A)ₓ−R¹ | M.p. (°C.) (recryst. from) | Preparation | Starting compound M.p. (°C.) | Preparation |
|---|---|---|---|---|---|---|---|
| 38 | Cl | 2-Cl-phenyl | −CH₃ | 152 | analogously to Example 1 | 151 (decomp.) | analogously to Example A4 |
| 39 | Cl | 3-Cl-phenyl | −CH₃ | 176 (decomp.) | analogously to Example 1 | 197 (decomp.) | analogously to Example A4 |
| 40 | Cl | 2,4-diCl-phenyl | −CH₃ | 197–8 | analogously to Example 1 | 188–9 (decomp.) | analogously to Example A4 |
| 41 | Cl | 3,5-diCl-phenyl | −CH₃ | 245 (decomp.) | analogously to Example 1 | 142–4 (decomp.) | analogously to Example A4 |
| 42 | Cl | 3-CH₃-phenyl | −CH₃ | 137–8 | see Example 1 | 175 (decomp.) | analogously to Example A4 |

-continued $$\underset{O_2N}{\overset{Hal}{\diagdown}}C=C\underset{S}{\overset{N}{\diagdown}}\underset{R}{\overset{}{N-C-(A)_x-R^1}}\quad (I)$$

| Compound No. | Hal | End products -R | -(A)$_x$-R$^1$ | M.p. (°C.) (recryst. from) | Preparation | Starting compound M.p. (°C.) | Preparation |
|---|---|---|---|---|---|---|---|
| 43 | Cl | 2,4-dimethylphenyl | -CH$_3$ | 167-8 | analogously to Example 1 | 177-8 (decomp.) | analogously to Example A4 |
| 44 | Cl | 3,5-dimethylphenyl | -CH$_3$ | 207 | analogously to Example 1 | 179-80 (decomp.) | analogously to Example A4 |
| 45 | Cl | 2,5-dimethylphenyl | -CH$_3$ | 169-70 | analogously to Example 1 | 183-5 (decomp.) | analogously to Example A4 |
| 46 | Cl | 2,6-dimethylphenyl | -CH$_3$ | 192-3 (decomp.) | analogously to Example 1 | 202 (decomp.) | analogously to Example A4 |
| 47 | Cl | 2-methoxyphenyl | -CH$_3$ | 176 | analogously to Example 1 | 185-6 (decomp.) | analogously to Example A4 |

-continued

| Compound No. | Hal | End products -R | -(A)ₓ-R¹ | M.p. (°C.) (recryst. from) | Preparation | Starting compound M.p. (°C.) | Preparation |
|---|---|---|---|---|---|---|---|
| 48 | Cl | 2,4-dimethylphenyl (CH₃, CH₃) | —CH₃ | 198 (decomp.) | analogously to Example 1 | 178-9 (decomp.) | analogously to Example A4 |
| 49 | Cl | 2-methylphenyl (CH₃) | —CH₃ | 156-7 | analogously to Example 1 | 180-1 (decomp.) | analogously to Example A4 |
| 50 | Cl | 4-bromophenyl (Br) | —CH₃ | 236 (decomp.) | analogously to Example 1 | 208 (decomp.) | Example A4 |
| 51 | Cl | 3-bromophenyl (Br) | —CH₃ | 162 | analogously to Example 1 | 191-2 (decomp.) | Example A4 |
| 52 | Cl | 4-(N,N-dimethylamino)phenyl (CH₃—N—CH₃) | —CH₃ | 151 | analogously to Example 1 | >260 | analogously to Example A4 |
| 53 | Cl | 2,5-dimethylphenyl (CH₃, CH₃) | —CH₃ | 158 | analogously to Example 1 | 186-7 (decomp.) | analogously to Example A4 |

-continued

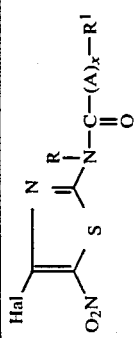
(I)

| Compound No. | Hal | End products —R | —(A)ₓ—R¹ | M.p. (°C.) (recryst. from) | Preparation | Starting compound M.p. (°C.) | Preparation |
|---|---|---|---|---|---|---|---|
| 54 | Cl | 3,5-dimethyl-4-methylphenyl (CH₃, CH₃, CH₃) | —CH₃ | 203 | analogously to Example 1 | 214–5 (decomp.) | analogously to Example A4 |
| 55 | Cl | 2,5-dimethoxy-4-methylphenyl (OCH₃, OCH₃, CH₃) | —CH₃ | 81–2 (decomp.) | analogously to Example 1 | 167–9 (decomp.) | analogously to Example A4 |
| 56 | Cl | 2-methoxy-4-methoxy-5-methylphenyl (OCH₃, OCH₃, CH₃) | —CH₃ | 221 | analogously to Example 1 | 153–4 (decomp.) | analogously to Example A4 |
| 57 | Cl | 2,5-dimethyl-3-methylphenyl (H₃C, CH₃, CH₃) | —CH₃ | 226 | analogously to Example 1 | 208–9 (decomp.) | analogously to Example A4 |
| 58 | Cl | 3-(isopropoxy)-methylphenyl (CH₃—CH—CH₃, O) | —CH₃ | 151 | analogously to Example 1 | 48–9 | analogously to Example A4 |

-continued

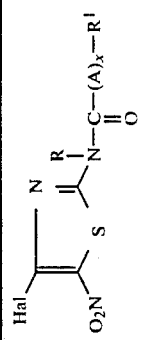

| Compound No. | Hal | End products —R | —(A)ₓ—R¹ | M.p. (°C.) (recryst. from) | Preparation | M.p. (°C.) | Starting compound Preparation |
|---|---|---|---|---|---|---|---|
| 59 | Cl | 2,4,5-trichlorophenyl | —CH₃ | 187-8 | analogously to Example 1 | 191-2 (decomp.) | analogously to Example A4 |
| 60 | Cl | 2-fluorophenyl | —CH₃ | 166 | analogously to Example 1 | 157-8 (decomp.) | analogously to Example A4 |
| 61 | Cl | 3-iodophenyl | —CH₃ | 147 | analogously to Example 1 | 158-9 (decomp.) | analogously to Example A4 |
| 62 | Cl | 4-acetoxyphenyl | —CH₃ | 197 | see Example 13 | 174-6 (decomp.) | analogously to Example A4 |
| 63 | Cl | 4-trifluoromethylphenyl | —CH₃ | 190-1 | analogously to Example 1 | 202-3 (decomp.) | analogously to Example A4 |
| 64 | Cl | 4-isopropylphenyl | —CH₃ | 148 (decomp.) | analogously to Example 1 | 161-2 (decomp.) | analogously to Example A4 |

-continued $$\underset{O_2N}{\overset{Hal}{\diagdown}}C=C\underset{S}{\overset{N}{\diagdown}}\underset{|}{\overset{R}{N}}-\underset{O}{\overset{\|}{C}}-(A)_x-R^1 \quad (I)$$

| Compound No. | Hal | End products —R | —(A)$_x$—R$^1$ | M.p. (°C.) (recryst. from) | Preparation | M.p. (°C.) | Starting compound Preparation |
|---|---|---|---|---|---|---|---|
| 65 | Cl | 4-I-C$_6$H$_4$ | —CH$_3$ | 260 (decomp.) | analogously to Example 1 | 165-6 (decomp.) | analogously to Example A4 |
| 66 | Cl | 3-CF$_3$-C$_6$H$_4$ | —CH$_3$ | 160 | analogously to Example 1 | 121-2 | analogously to Example A4 |
| 67 | Cl | 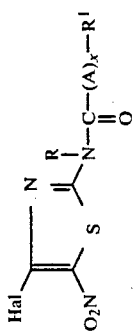 | —CH$_3$ | 201 (decomp.) | analogously to Example 1 | 226-7 | analogously to Example A4 |
| 68 | Cl | 2-Br-C$_6$H$_4$ | —CH$_3$ | 122-3 | analogously to Example 1 | 157-8 (decomp.) | analogously to Example A4 |
| 69 | Cl | 4-SCF$_3$-C$_6$H$_4$ | —CH$_3$ | 130-1 | analogously to Example 1 | 126 (decomp.) | analogously to Example A4 |
| 70 | Cl | —CH$_3$ | 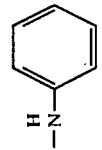 | 225 (decomp.) | see Example 4 | 212 (decomp.) | see Example A8 |

-continued

(I)

| Compound No. | Hal | End products -R | -(A)ₓ-R¹ | M.p. (°C.) (recryst. from) | Preparation | Starting compound M.p. (°C.) | Preparation |
|---|---|---|---|---|---|---|---|
| 71 | Cl | SCF₃ (2-SCF₃-phenyl) | —CH₃ | 135 | analogously to Example 1 | 126-7 (decomp.) | analogously to Example A4 |
| 72 | Cl | 2,6-dichlorophenyl (with Cl at 4) | —CH₃ | 142 | analogously to Example 1 | 221 (decomp.) | analogously to Example A4 |
| 73 | Cl | 2,4,6-trimethoxyphenyl | —CH₃ | 226 (decomp.) | analogously to Example 1 | 177-8 (decomp.) | analogously to Example A4 |
| 74 | Cl | 2-OCH₃-phenyl | —CH₃ | 111 | analogously to Example 1 | 201 (decomp.) | analogously to Example A4 |
| 75 | Cl | 2,6-diisopropylphenyl | —CH₃ | 114 | analogously to Example 1 | 228 (decomp.) | analogously to Example A4 |

-continued

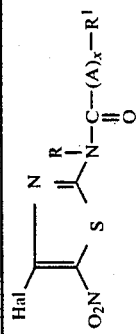
(I)

| Compound No. | Hal | End products -R | -(A)ₓ-R¹ | M.p. (°C.) (recryst. from) | Preparation | M.p. (°C.) | Starting compound Preparation |
|---|---|---|---|---|---|---|---|
| 76 | Cl | 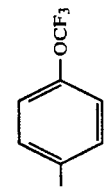 | —CH₃ | 157 | analogously to Example 1 | 121 (decomp.) | analogously to Example A4 |
| 77 | Cl | 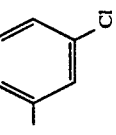 | —CH₃ | 164 | analogously to Example 1 | 136-8 (decomp.) | analogously to Example A4 |
| 78 | Cl | 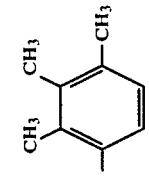 | —CH₃ | 232-3 (decomp.) | analogously to Example 1 | 194 (decomp.) | analogously to Example A4 |
| 79 | Cl | 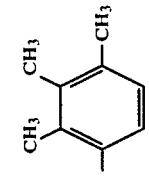 | —CH₃ | 172-3 | analogously to Example 1 | 216-7 (decomp.) | analogously to Example A4 |
| 80 | Cl | 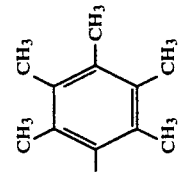 | —CH₃ | 260 (decomp.) | analogously to Example 1 | 243-4 (decomp.) | analogously to Example A4 |
| 81 | Cl | 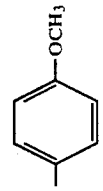 | —CH₃ | 169-70 | analogously to Example 1 | 193 (decomp.) | analogously to Example A4 |

-continued (I)

| Compound No. | End products Hal | -R | -(A)ₓ-R¹ | M.p. (°C.) (recryst. from) | Preparation | Starting compound M.p. (°C.) | Preparation |
|---|---|---|---|---|---|---|---|
| 82 | Cl | 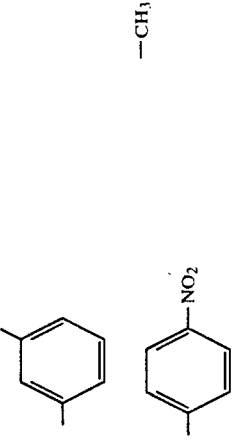 (3-OCH₃-C₆H₄) | -CH₃ | 197 | analogously to Example 1 | 175-6 (decomp.) | analogously to Example A4 |
| 83 | Cl | 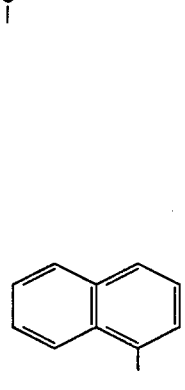 (4-NO₂-C₆H₄) | -CH₃ | 142 | analogously to Example 1 | 262-3 (decomp.) | analogously to Example A4 |
| 84 | Cl |  (1-naphthyl) | -CH₃ | 227-8 (decomp.) | analogously to Example 1 | 178-9 (decomp.) | analogously to Example A4 |
| 85 | Cl |  | -CH₃ | 246-7 (decomp.) | see Example 11 | 203 (decomp.) | analogously to Example A4 |
| 86 | Cl |  (2-CF₃-4-Cl-C₆H₃) | -CH₃ | 224 (decomp.) | analogously to Example 1 | 124-5 (decomp.) | analogously to Example A4 |
| 87 | Cl | 3-NO₂-C₆H₄ | -CH₃ | 213 (decomp.) | analogously to Example 1 | 163-4 (decomp.) | analogously to Example A4 |

-continued $$\underset{O_2N}{\overset{Hal}{\diagdown}}C=C\underset{S}{\overset{N}{\diagup}}\underset{\overset{|}{R}}{\underset{|}{N}}-\underset{\overset{\|}{O}}{C}-(A)_x-R^1 \quad (I)$$

| Compound No. | End products Hal | —R | —(A)$_x$—R$^1$ | M.p. (°C.) (recryst. from) | Preparation | Starting compound M.p. (°C.) | Preparation |
|---|---|---|---|---|---|---|---|
| 88 | Cl | N(CH₃)₂ — [3-methylphenyl] | —CH₃ | 226 (decomp.) | analogously to Example 1 | 169–70 (decomp.) | analogously to Example A4 |
| 89 | Cl | CONH₂ — [4-phenyl] | —CH₃ | 154-5 | analogously to Example 1 | 259 (decomp.) | analogously to Example A4 |
| 90 | Cl | C(=O)—CH₃ — [4-phenyl] | —CH₃ | 187-8 | analogously to Example 1 | 262-3 (decomp.) | analogously to Example A4 |
| 91 | Cl | SO₂N(H)—C(=O)—CH₃ — [4-phenyl] | —CH₃ | 244 (decomp.) | see Example 14 | >280 | analogously to Example A4 |
| 92 | Cl | C₂H₅ — [4-phenyl] | —CH₃ | 177-9 | analogously to Example 1 | 174-5 (decomp.) | analogously to Example A4 |
| 93 | Cl | SO₂—CH₃ — [4-phenyl] | —CH₃ | 255-6 (decomp.) | analogously to Example 1 | 268-9 (decomp.) | analogously to Example A4 |
| 94 | Cl | O—(CH₂)₃—CH₃ — [4-phenyl] | —CH₃ | 88 | analogously to Example 1 | 154-5 (decomp.) | analogously to Example A4 |

-continued $$\begin{array}{c} Hal \\ | \\ O_2N \end{array} \!\! = \!\! \begin{array}{c} N \\ | \\ S \end{array} \!\! N \!\! - \!\! \begin{array}{c} R \\ | \\ C \!\! - \!\! (A)_x \!\! - \!\! R^1 \\ \| \\ O \end{array} \quad (I)$$

| Compound No. | End products Hal | —R | —(A)$_x$—R$^1$ | M.p. (°C.) (recryst. from) | Preparation | M.p. (°C.) | Starting compound Preparation |
|---|---|---|---|---|---|---|---|
| 95 | Cl | 4-methylphenyl-cyclohexyl (H) | —CH$_3$ | 155–6 | analogously to Example 1 | 185–6 (decomp.) | analogously to Example A4 |
| 96 | Cl | —C$_2$H$_5$ | —CH$_3$ | 109 | analogously to Example 1 | 167–8 (decomp.) | analogously to Example A8 |
| 97 | Cl | —CH$_2$—C$_2$H$_5$ | —CH$_3$ | 120–1 | analogously to Example 1 | ab 106 (decomp.) | analogously to Example A8 |
| 98 | Cl | —CH$_2$—CH$_2$—OCH$_3$ | —CH$_3$ | 115–6 | analogously to Example 1 | 124–8 (decomp.) | analogously to Example A8 |
| 99 | Cl | —CH$_2$—CH$_2$—Cl | —CH$_3$ | 95–6 | analogously to Example 1 | 143–4 (decomp.) | analogously to Example A8 |
| 100 | Cl | —CH$_2$—CH=CH$_2$ | —CH$_3$ | 63–4 | analogously to Example 1 | 130 | analogously to Example A4 |
| 101 | Cl | CH$_3$<br>—CH— phenyl | —CH$_3$ | 117–8 (decomp.) | see Example 7 | 108 | analogously to Example A4 |
| 102 | Cl | CH$_3$<br>—CH—CH$_3$ | —CH$_3$ | 131–3 | analogously to Example 7 | 125–7 (decomp.) | analogously to Example A8 |
| 103 | Cl | 2,6-dichlorophenyl | —CH$_3$ | 95 | see Example 15 | 141 | see Example A11 |
| 104 | Cl | —CH$_3$ | —OCH$_3$ | 157–8 | see Example 9 | 130–1 | see Example A9 |

-continued $$\begin{array}{c} \text{Hal} \\ \diagdown \\ \text{O}_2\text{N} \end{array} \diagup \begin{array}{c} \text{N} \\ \diagdown \\ \text{S} \end{array} \diagup \begin{array}{c} \text{R} \\ \diagdown \\ \text{N}-\text{C}-(\text{A})_x-\text{R}^1 \\ \parallel \\ \text{O} \end{array} \quad (I)$$

| Compound No. | Hal | End products −R | −(A)ₓ−R¹ | M.p. (°C.) (recryst. from) | Preparation | M.p. (°C.) | Starting compound Preparation |
|---|---|---|---|---|---|---|---|
| 105 | Cl | −CH₃ | −S−⟨C₆H₄⟩−OCH₃ | 183−4 | see Example 10 | 130−1 | see Example A9 |
| 106 | Cl | −CH₃ | −OCH(CH₃)CH₃ | 116−8 | analogously to Example 9 | 130−1 | see Example A9 |
| 107 | Cl |  −N−C−(A)ₓ−R¹: | pyrrolidinone ring | 172.5−173 (cyclohexane) | see Example 16 |  |  |
| 108 | Cl | −CH₃ | piperidinyl | 168−71 (decomp.) | see Example 17 and Example 18 | 30−1 212 (decomp.) | see Example A9 see Example A8 |
| 109 | Cl | −CH₃ | −NH₂ | 191−2 | analogously to Example 8 | 130−1 | see Example A9 |
| 110 | Cl | −CH₃ | −S−CH₂−COOC₂H₅ | 109 | analogously to Example 10 | 130−1 | see Example A9 |
| 111 | Cl | −CH₃ | −O−⟨C₆H₄⟩−F | 199 | analogously to Example 10 | 130−1 | see Example A9 |
| 112 | Cl | −CH₃ | −N(CH₃)−C₆H₅ | 165−6 | analogously to Example 10 | 130−1 | see Example A9 |

-continued $$\begin{array}{c} Hal \\ \diagdown \\ O_2N \end{array} C = C \begin{array}{c} N \\ \diagdown \\ S \end{array} \begin{array}{c} R \\ \diagdown \\ N-C-(A)_x-R^1 \\ \| \\ O \end{array} \quad (I)$$

| Compound No. | Hal | End products R | —(A)ₓ—R¹ | M.p. (°C.) (recryst. from) | Preparation | M.p. (°C.) | Starting compound Preparation |
|---|---|---|---|---|---|---|---|
| 113 | Cl | —CH₃ | 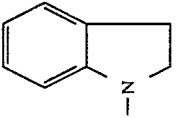 | 181–2 (decomp.) | analogously to Example 10 | 130–1 | see Example 9 |
| 114 | Cl | —CH₃ | 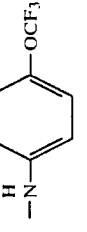 | 209 (decomp.) | analogously to Example 10 | 130–1 | see Example A9 |
| 115 | Cl | —CH₃ | 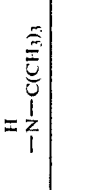 H —N—C(CH₃)₃ | 158–60 (decomp.) | analogously to Example 10 | 130–1 | see Example A9 |

(decomp.) = with decomposition

USE EXAMPLES

EXAMPLE A

*Cochiobolus sativus* test (barley)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Cochiobolus sativus*. The plants remain for 48 hours in an incubation cabin at 20° C. and 100% relative atmospheric humidity.

The plants are placed in a greenhouse at a temperature of about 20° C. and a relative atmospheric humidity of about 80%.

Evaluation is effected 7 days after the inoculation.

For example, Compounds Nos. 3, 5, 9, 25, 27, 29, 32 and 35, show a degree of effectiveness of between 70 and 85% at an active compound concentration of 0.025% by weight in the spray liquor.

EXAMPLE B

*Leptoshaeria nodorum* test (wheat)/protective
Solvent: 100 parts by weight of dimethylformamide
Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a spore suspension of *Leptoshaeria nodorum*. The plants remain for 48 in an incubation cabin at 20° C. and 100% relative atmospheric humidity.

The plants are placed in a greenhouse at a temperature of about 15° C. and a relative atmospheric humidity of about 80%.

Evaluation is effected 10 days after the inoculation.

Compounds Nos. 2, 3, 4, 13, 5, 8, 9, 24 and 34 show a degree of effectiveness of between 70 and 85% at an active compound concentration of 0.025% by weight in the spray liquor.

EXAMPLE C

Phytophthora test (tomato)/protective
Solvent: 4.7 parts by weight of acetone
Emulsifier: 0.3 parts by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound to run-off point. After the spray coating has dried on, the plants are inoculated with an aqueous spore suspension of Phytophthora infestans.

The plants are placed in an incubation cabin at 100% relative atmospheric humidity and at about 20° C.

Evaluation is carried out 3 days after the inoculation.

At an active compound concentration of 10 ppm, the Compounds Nos. 10, 13, 17, 16 and 18 show a degree of effectiveness of between 50 and 75%.

EXAMPLE D

To demonstrate the effectiveness against fungi, the minimum inhibitory concentrations (MICs) of active compounds according to the invention are determined:

Active compounds according to the invention are added in concentrations of 0.1 mg/l to 500 mg/l to an agar which is prepared from brewer's wort and peptone. After the agar has solidified, it is contaminated with pure-bread cultures of the test organisms listed below. The agar is stored for two weeks at 28° C. and 60 to 70% relative atmospheric humidity, and the MIC is then determined. MIC is the lowest concentration of active compound where no growth whatsoever of the microbe species used is observed on the agar.

For example the Compounds Nos. 20, 25, 3, 13, 17, 15, 24, 2, 23, 12, 16 and 26 show a good activity in this test.

Test organisms:
*Alternaria tenuis*
*Aspergillus niger*
*Aureobasidium pullulans*
*Chaetomium globosum*
*Cladosporium cladosporioides*
*Lentinum tigrinus*
*Penicillium glaucum*
*Sclerophoma pityophila*

It is understood that the specification and examples are illustrative but not limitative of the present invention and that other embodiments within the spirit and scope of the invention will suggest themselves to those skilled in the art.

We claim:

1. A 2-acylamino-4-halogeno-5-nitrothiazole of the formula

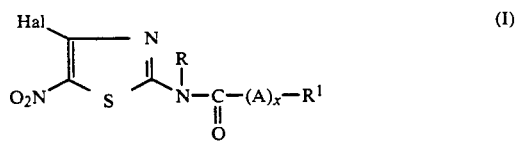

in which
Hal represents chlorine, bromine or iodine,
x represents an integer 0 or 1,
A represents O, S or NR$^2$, where R$^2$ represents hydrogen, alkyl having 1 to 4 carbon atoms, alkenyl having 3 to 5 carbon atoms, halogenoalkyl having 1 to 3 carbon atoms and 1 to 5 identical or different halogen atoms, or represents cyanoalkyl having 1 or 2 carbon atoms in the alkyl moiety, or represents alkoxycarbonylalkyl having 1 to 4 carbon atoms in each the alkoxy and alkyl moiety, or represents cycloalkyl having 3 to 6 carbon atoms, or represents phenyl or phenylalkyl, each of which is optionally monosubstituted to trisubstituted by identical or different substituents from the group consisting of alkyl having 1 to 4 carbon atoms, fluorine, chlorine, bromine and alkoxy having 1 to 4 carbon atoms, where phenylalkyl has 1 to 3 carbon atoms in the alkyl moiety, and R represents hydrogen, alkyl having 1 to 12 carbon atoms, alkenyl having up to 12 carbon atoms, alkinyl having up to 12 carbon atoms, or alogenoalkyl, halogenoalkenyl or halogenoalkinyl, each of which has up to 8 carbon atoms and 1 to 10 identical or different halogen atoms, or represents alkoxyalkyl, alkylmercaptoalkyl or cyanoalkyl, each of which has 1 to 4 carbon atoms per alkyl, alkoxy or alkylthio moiety, respectively, or represents phenyloxyalkyl or phenylmercaptoalkyl, each of which has 1 to 4 carbon atoms in the alkyl moiety, it being possible for the phenyl radicals to be optionally mobosubstituted to trisubstituted by identical or different substituents from the group consisting of fluorine, chlorine, bromine and alkyl having 1 to 4 carbon atoms, or represents cycloalkyl which has 3 to 8 carbon atoms and which is optionally monosubstituted to trisubstituted by identical or different alkyl substituents having 1 to 4 carbon atoms, it being possible for the cycloalkyl ring to additionally contain a fused-on benzene ring, or represents phenylalkyl which has 1 to 4 carbon atoms in the alkyl moiety and which is optionally monosubstituted to pentasubstituted by identical or different substituents from the group consisting of halogen, alkyl having 1 to 4 carbon atoms, halogenoalkyl having 1 to 4 carbon atoms and 1 to 8 identical of different halogen atoms, nitro, cyano, alkoxy having 1 to 4 carbon atoms and alkylmercapto having 1 to 4 carbon atoms, it being possible for the alkyl moiety to optionally contain a further phenyl radical as a substituent which can optionally also be substituted as recited above, or represents phenyl which is optionally monosubstituted to pentasubstituted by identical or different substituents from the group consisting of halogen, nitro, alkenyl or alkinyl, in each case having up to 5 carbon atoms, alkyl, alkoxy, alkylmercapto, carbalkoxy, alklsulphonylamino, alkylsulphonyl, sulphamoyl, N-alkylsulphamoyl, N-N-dialkysulphamoyl, dialkylamino, carbamoyl, N-alkylcarbamoyl or N-N-dialkylcarbamoyl, in each case having 1 to 4 carbon atoms per alkyl radical, halogenoalkyl, halogenoalkoxy or halogenoalkylmercapto, in each case having 1 to 4 carbon atoms and 1 to 8 identical or different halogen atoms per listed radical, phenyl, phenoxy, phenylmercapto, acyloxy having 1 to 3 carbon atoms, acyl having 1 to 3 carbon atoms, phenylalkyloxy have 1 to 3 carbon atoms in the alkyl moiety, phenylalkylmercapto having 1 to 3 carbon atoms, acylamino having 1 to 3 carbon atoms, acylalkylamino, N-acylalkylsulphamoyl or acylaminosulphonyl, in each case having 1 to 3 carbon atoms per acyl and alkyl radical, cycloalkyl having 4 to 6 carbon atoms and cyano, or represents naphthyl, $R^1$ represents hydrogen, alkyl having 1 to 6 carbon atoms, alkenyl or alkinyl, in each case having 3 to 5 carbon atoms, halogenoalkyl having 1 to 5 carbon atoms and 1 to 8 identical or different halogen atoms, cyanoalkyl having 1 or 2 carbon atoms in the alkyl moiety, alkoxycarbonylalkyl having 1 to 4 carbon atoms in each alkoxy and alkyl moiety, or represents cycloalky which has 3 to 6 carbon atoms and which is optionally monosubstituted to trisubstituted by alkyl having 1 to 3 carbon atoms, or represents phenyl or phenylalkyl, each of which is optionally monosubstituted to trisubstituted by identical or different alkyl substituents having 1 to 4 carbon atoms or by fluorine, chlorine, bromine or alkoxy, halogenoalkyl or halogenoalkoxy, in each case having 1 to 4 carbon atoms and where appropriate 1 to 5 identical or different halogen atoms, where phenylalkyl has 1 to 3 carbon atoms in the alkyl moiety, or $R^1$ represents heterocyclyl or heterocyclyalkyl, each of which has 1 to 4 carbon atoms in the alkyl moiety and 5 to 7 ring members in the heterocyclyl moiety which can contain one to three identical or different hetero atoms, and to which benzene rings may be fused, it being possible for each of the rings to be optionally monosubstituted to trisubstituted by identical or different substituents from the group consisting of halogen, alkyl having 1 to 4 carbon atoms and alkoxy having 1 to 3 carbon atoms, or R and $R^1$ together with the group —N—CO—$(A)_x$—, at which they are located form a ring which has 5 to 7 ring members and which can optionally contain one or two further nitrogen and/or oxygen atoms and which can optionally be monosubstituted to trisubstituted by alkyl having 1 to 4 carbon atoms, or $R^1$ and $R^2$ together with the nitrogen atom at which they are located form a ring which has 5 to 7 ring members and which can optionally contain one or two further nitrogen and/or oxygen atoms and which can optionally be monosubstituted to trisubstituted by alkyl having 1 to 4 carbon atoms and where, if appropriate, benzene rings can be fused on, with the exception that $R^1$ is not hydrogen when A represents O or S, and the compound 2-acetylamino-4-iodo-5-nitro-thiazole being excepted.

2. A 2-acylamino-4 halogeno-5-nitrothiazole according to claim 1, in which

Hal represents chlorine, x represents 0,

R represents hydrogen, straight-chain or branched alkyl having 1 to 6 carbon atoms, straight-chain or branched alkenyl having up to 6 carbon atoms, halogenoalkyl having 1 to 4 carbon atoms and 1 to 6 identical or different halogen atoms, alkoxyalkyl in each case having 1 to 3 carbon atoms in each alkoxy or alkyl moeity, R furthermore represents cyclohexyl, naphthyl, phenylalkyl which has 1 to 4 carbon atoms in the straight-chain or branched alkyl moiety and which is optionally monosubstituted to trisubstituted by identical or different substitutents from the group consisting of alkyl having 1 to 3 carbon atoms and halogen, or represents phenyl which is optionally monosubstituted to pentasubstituted by identical or different alkyl substitutents having 1 to 3 carbon atoms or which is optionally monosubstituted to trisubstituted by identical or different substitutents from the group consisting of halogen, nitro, cyclohexyl, alkyl having 1 to 4 carbon atoms, alkoxy having 1 to 4 carbon atoms, alkylsulphonyl having 1 to 4 carbon atoms, dialkylamino having 1 to 4 carbon atoms per alkyl moiety, carbamoyl, N-alylcarbamonyl or N-N-dialkyl-carbamoyl, each of which has 1 to 4 carbon atoms per alkyl moiety, halogenoalkoxy or halogenoalkylmercapto, in each case having 1 to 4 carbon atoms and 1 to 5 identical or different halogen atoms, acyl or acylamino, in each case having 1 to 3 carbon atoms, acyloxy having 1 to 3 carbon atoms, and N-acyl-alkylsulphamoyl or acylaminosulphonyl, in each case having 1 to 3 carbon atoms per acyl and alkyl moiety, and $R^1$ represents alkyl having 1 to 6 carbon atoms, halogenoalkyl having 1 to 3 carbon atoms and 1 to 5 identical or different halogen atoms, or represents cyclohexyl which is optionally monosubstituted to trisubstituted by methyl, ethyl or propyl, or represents phenyl which is optionally monosubstituted to trisubstituted in each case by identical or different substitutents from the group consisting of alkyl having 1 to 3 carbon atoms, fluorine, chlorine, bromine, alkoxy, halogenoalkyl or halogenoalkoxy having 1 to 3 carbon atoms in each case and where appropriate 1 to 5 identical or different halogen atoms, or $R^1$ represents a 4- or 6-membered ring which has 1 to 3 identical or different hetero atoms and which is optionally monosubstituted to trisubstituted by identical or different substituents from the group consisting of chlorine, methyl, ethyl, n- or isopropyl, the compound 2-acetyl-amino-4-iodo-5-nitro-thiazole being excepted.

3. A 2-acylamino-4halogeno-5-nitrothiazole according to claim 1, in which

R represents hydrogen, straight-chain or branched alkyl having 1 to 6 carbon atoms, straight-chain or branched alkenyl having up to 6 carbon atoms, halogenoalkyl having 1 to 4 carbon atoms and 1 to 6 identical or different halogen atoms, alkoxyalkyl in each case having 1 to 3 carbon atoms in each the alkoxy and alkyl moiety, R furthermore represents cyclohexyl, naphthyl, phenylalkyl which has 1 to 4 carbon atoms in the straight-chain or branched alkyl moiety and which is optionally monosubstituted to trisubstituted by identical or different substituents from the group consisting of alkyl having 1 to 3 carbon atoms and halogen, or represents phenyl which is optionally monosubstituted to pentasubstituted by identical or different alkyl substituents having 1 to 3 carbon atoms or which is optionally monosubstituted to trisubstituted by identical or different substituents from the group consisting of halogen, nitro, cyclohexyl, alkyl having 1 to 4 carbon atoms, alkoxy having 1 to 4 carbon atoms, alkylsulphonyl having 1 to 4 carbon atoms, dialkylamino having 1 to 4 carbon atoms per alkyl moiety, carbamoyl, N-alkylcarbamoyl or N,N-dialkyl-carbamoyl having 1 to 4 carbon atoms per alkyl moiety, halogenoalkoxy or halogenoalkylmercapto, in each case having 1 to 4 carbon atoms and 1 to 5 identical or different halogen atoms, acyl or acylamino, in each case having 1 to 3 carbon atoms, acyloxy having 1 to 3 carbon atoms, and N-acylalkysulphamoyl or acylaminosulphonyl, in each case having 1 to 3 carbon atoms per acyl and alkyl moiety, and x represents 1, A represents O or S and $R^1$ represents alkyl having 1 to 4 carbon atoms, or represents phenyl which is optionally monosubstituted to trisubstituted by identical or different substituents from the group consisting of halogen, alkoxy, alkyl, halogenoalkyl and halogenoalkoxy, in each case having 1 to 3 carbon toms and where appropriate 1 to 5 identical or different halogen atoms, or $R^1$ represents a 5- or 6-membered ring having 1 or 2 identical or different hetero atoms, or R and $R^1$ with the group —N—CO—(A)$_x$— at which they are located form a 5- or 6- membered ring which can optionally be monosubstituted to trisubstituted by identical or different substituents from the group consisting of halogen and alkyl having 1 to 4 carbon atoms.

4. A 2-acylamino-4-halogeno-5-nitrothiazole according to claim 1, in which

R represents hydrogen, straight-chain or branched alkyl having 1 to 6 carbon atoms, straight-chain or branched alkenyl having up to 6 carbon atoms, halogenoalkyl having 1 to 4 carbon atoms and 1 to 6 identical or different halogen atoms, alkoxyalkyl in each case having 1 to 3 carbon atoms in each alkoxy and alkyl moiety, R furthermore represents cyclohexyl, naphthyl, phenyalkyl which has 1 to 4 carbon atoms in the straight-chain or branched alkyl moiety and which is optionally monosubstituted to trisubstituted by identical or different substituents from the group consisting of alkyl having 1 to 3 carbon atoms and halogen, or represents phenyl which is optionally monosubstituted to pentasubstituted by identical or different alkyl substituents having 1 to 3 carbon atoms or which is optionally monosubstituted to trisubstituted by identical or different substituents from the group consisting of halogen, nitro, cyclohexyl, alkyl having 1 to 4 carbon atoms, alkoxy having 1 to 4 carbon atoms, alkysulphonyl having 1 to 4 carbon atoms, dialkylamino having 1 to 4 carbon atoms per alkyl moiety, carbamoyl, N-alkyl-carbamoyl or N,N-dialkyl-carbamoyl having 1 to 4 carbon atoms per alykl moiety, halogenoalkoxy or halogenoalkylmercapto, in each case having 1 to 4 carbon atoms and 1 to 5 identical or different halogen atoms, acyl or acylamino, in each case having 1 to 3 carbon atoms, acyloxy having 1 to 3 carbon atoms, or N-acylalkylsulphamoyl or acylaminosulphonyl, in each case having 1 to 3 carbon atoms per acyl and alkyl moiety, and x represents 1, A represents $NR^2$, $R^1$ represents hydrogen, alkyl having 1 to 6 carbon atoms, halogenoalkyl having 1 to 3 carbon atoms and 1 to 5 identical or different halogen atoms, or represents cyclohexyl which is optionally monosubstituted to trisubstituted by methyl, ethyl or propyl, or represents phenyl which is optionally monosubstituted to trisubstituted in each case by identical or different substituents from the group consisting of alkyl having 1 to 3 carbon atoms, fluorine, chlorine, bromine, alkoxy, halogenoalkyl or halogenoalkoxy, in each case having 1 to 3 carbon atoms and where appropriate 1 to 5 identical or different halogen atoms, or represents a 5- or 6- membered ring which has 1 to 3 identical or different nitrogen, sulphur and/or oxygen ring atoms and which is optionally monosubstituted to trisubstituted by identical or different substituents from the group consisting of chlorine, methyl, ethyl and n- or isopropyl, and $R^2$ represents hydrogen, alkyl having 1 to 4 carbon atoms, alkenyl having 3 to 5 carbon atoms, halogenoalkyl having 1 to 3 carbon atoms and 1 to 5 identical or different halogen atoms, or represents cyanoalkyl having 1 or 2 carbon atoms in the alkyl moiety, or represents cycloalkyl having 3 to 6 carbon atoms, or represents phenyl or phenylalkyl, each of which is optionally monosubstituted to trisubstituted by identical or different substituents from the group consisting of alkyl having 1 to 4 carbon atoms, fluorine, chlorine, bromine and alkoxy having 1 to 4 carbon atoms, where phenylalkyl has 1 to 3 carbon atoms in the alkyl moiety, and R$^1$ and R$^2$ together with the nitrogen atom at which they are located form a ring having 5 to 7 ring members which can optionally contain one or two further nitrogen and/or oxygen atoms and which can be optionally monosubstituted to trisubstituted by alkyl having 1 to 4 carbon atoms, and further rings can be fused on, with the exception of the compound 2-acetylamino-4-iodo-5nitro-thiazole.

5. A compound according to claim 1, wherein such compound is N-methyl-N$^1$-methyl-N$^1$-(4-chloro-5-nitro-thiazol-2-yl)-urea of the formula

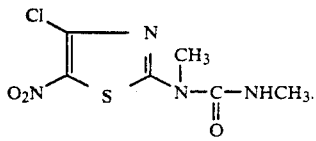

6. A compound according to claim 1, wherein such compound is 2-(acetyl-methylamino)-4-chloro-5-nitro-thiazole of the formula

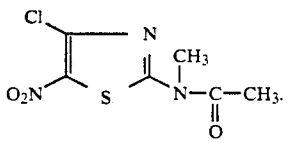

7. A compound according to claim 1, wherein such compound is 2-(propionyl-methylamino)-4chloro-5-nitro-thiazole of the formula

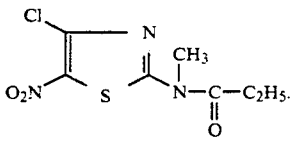

8. A compound according to claim 1, wherein such compound is 2-(propionyl-anilino)-4-chloro-5-nitro-thiazole of the formula

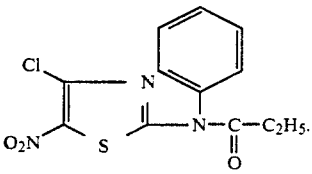

9. A compound according to claim 1, wherein such compound is 2-(acetyl-4-fluoroanilino)-4-chloro-5-nitro-thiazole of the formula

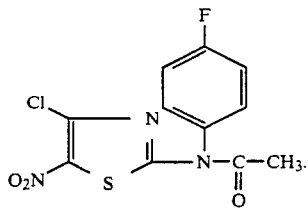

10. A compound according to claim 1, wherein such compound is 2-(chloroacetyl-methylamino)-4-chloro-5-nitrothiazole of the formula

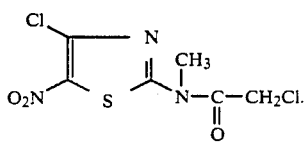

11. A compound according to claim 1, wherein such compound is 2-(trichloroacetyl-methylamino)-4-chloro-5-nitro-thiazole of the formula

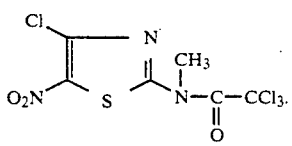

12. A compound according to claim 1, wherein such compound is 2-(dichloroacetyl-anilino)-4chloro-5-nitro-thiazole of the formula

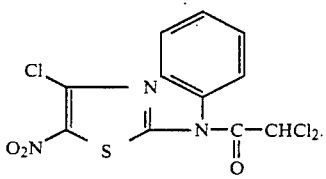

13. A compound according to claim 1, wherein such compound is 2-(dichloroacetyl-methylamino)-4-chloro-5- nitro-thiazole of the formula

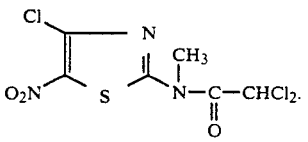

14. A compound according to claim 1, wherein such compound is 2-[N-(2,4-dichloro-thiazol-5-yl)-carbonyl)N-methylamino]-4-chloro-5-nitro-thiazole of the formula

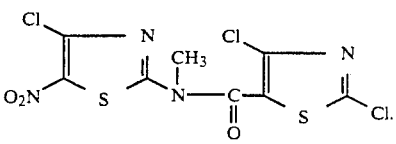

15. A compound according to claim 1, wherein such compound is 2-(butyryl-methylamino)-4-chloro-5-nitrothiazole of the formula

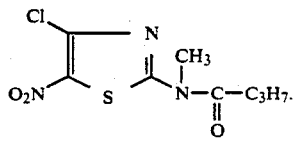

16. A compound according to claim 1, wherein such compound is 2-(propionyl-propylamino)-4-chloro-5-nitrothiazole of the formula

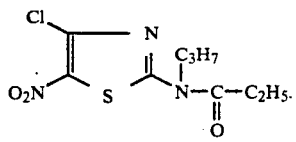

17. A fungicidal or microbicidal composition comprising a fungicidally or microbicidally effective amount of a compound according to claim 1 and a diluent.

18. A method of combating fungi and microbes which comprises applying to such fungi or microbes or to a locus from which it is desired to exclude such fungi or microbes a fungicidally or microbicidally effective amount of a compound according to claim 1.

19. The method according to claim 18, wherein such compound is
N-methyl-$N^1$-methyl-$N^1$-(chloro-5-nitro-thiazol-2-yl)-urea,
2-(acetyl-methylamino)-4-chloro-5-nitro-thiazole,
2-(propionyl-methylamino)-4-chloro-5-nitrothiazole,
2-(propionyl-anilino)-4-chloro-5-nitro-thiazole,
2-(acetyl-4-fluoroanilino)-4-chloro-5-nitrothiazole,
2-(chloroacetyl-methylamino)-4-chloro-5-nitrothiazole,
2-(trichloroacetyl-methylamino)-4-chloro-5-nitrothiazole,
2-(dichloroacetyl-anilino)4-chloro-5-nitrothiazole,
2-(dichloroacetyl-methylamino)4-chloro-5-nitrothiazole,
2[N-(2,4-dichloro-thiazol-5-yl)-carbonyl)-N-methylamino]-4-chloro-5-nitro-thiazole,
2-(butyryl-methylamino)-4-chloro-5-nitrothiazole or
2-(propionyl-propylamino)-4-chloro-5- nitrothiazole.

20. A 4-halogeno-2-halogenocarbonylamino-5-nitrothiazole of the formula

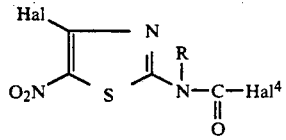

(VIII)

in which
Hal represents chlorine, bromine, or iodine, and
R represents alkyl having 1 to 12 carbon atoms, alkenyl having up to 12 carbon atoms, alkinyl having up to 12 carbon atoms, or halogenoalkyl, halogenoalkenyl or halogenoalkinyl, each of which has up to 8 carbon atoms and 1 to 10 identical or different halogen atoms, or represents alkoxyalkyl, alkylmercaptoalkyl or cyanoalkyl, each of which has 1 to 4 carbon atoms per alkly, alkoxy or alkylthio moiety, respectively, or represents phenyloxyalkyl or phenylmercaptoalkyl, each of which has 1 to 4 carbon atoms in the alkyl moiety, it being possible for the phenyl radicals to be optionally monosubstituted to trisubstituted by identical or different substituents from the group consisting of fluorine, chlorine, bromine and alkyl having 1 to 4 carbon atoms, or represents cycloalkyl which has 3 to 8 carbon atoms and which is optionally monosubstituted to trisubstituted by identical or different alkyl substituents having 1 to 4 carbon atoms, it being possible for the cycloakyl ring to additionally contain a fused-on benzene ring, or represents phenylalkyl which has 1 to 4 carbon atoms in the alkyl moiety and which is optionally monosubstituted to pentasubstituted by identical or different substituents from the group consisting of halogen, alkyl having 1 to 4 carbon atoms, halogenoalkyl having 1 to 4 carbon atoms and 1 to 8 identical or different halogen atoms, nitro, cyano, alkoxy having 1 to 4 carbon atoms and alkylmercapto having 1 to 4 carbon atoms, it being possible for the alkyl moiety to optionally contain a further phenyl radical as a substituent which can optionally also be substituted as recited above, or represents phenyl which is optionally monosubstituted to pentasubstituted by identical or different substituents from the group consisting of halogen, nitro, alkenyl or alkinyl, in each case having up to 5 carbon atoms, alkyl, alkoxy, alkylmercapto, carbalkoxy, alkysulphonylamino, alkylsulphonyl, sulphamoyl, N-alkysulphamoyl, N-N-dialkylsulphamoyl, dialkyamino, carbamoyl, N-alkylcarbamoyl or N,N-dialkylcarbamoyl, in each case having 1 to 4 carbon atoms per alkyl radical, halogenoalkyl, halogenoalkoxy or halogenoalkylmercapto, in each case having 1 to 4 carbon atoms and 1 to 8 identical or different halogen atoms per listed radical, phenyl, phenoxy, phenylmercapto, acyloxy having 1 to 3 carbon atoms, acyl having 1 to 3 carbon atoms, phenylalkyloxy having 1 to 3 carbon atoms in the alkyl moiety, phenylalkylmercapto having 1 to 3 carbon atoms, acylamino having 1 to 3 carbon atoms, acylalkylamino, N-acylalkylsulphamoyl or acylaminosulphonyl, in each case having 1 to 3 carbon atoms per acyl and alkyl radical, cycloalkyl having 4 to 6 carbon atoms and cyano, or represents naphthyl.

* * * * *

UNITED STATES PATENT AND TRADEMARK OFFICE
CERTIFICATE OF CORRECTION

PATENT NO. : 5,071,865  Page 1 of 2
DATED : December 10, 1991
INVENTOR(S) : Beck, et al It is certified that error appears in the above-indentified patent and that said Letters Patent is hereby corrected as shown below:

| | |
|---|---|
| Col. 71, line 5 | Delete " alogenoalkyl " and substitute -- halogeno-alkyl -- |
| Col. 71, line 29 | Delete " of " and substitute -- or -- |
| Col. 71, lines 40-41 | Delete " alklsulphonylamino " and substitute alkylsulphonylamino -- |
| Col. 72, line 10 | Delete " heterocyclyalkyl " and substitute -- hetero-cyclylalkyl -- |
| Col. 72, line 48 | Delete " moeity " and substitute -- moiety -- |
| Col. 72, line 64 | Delete " N-alylcarbamoyl " and substitute -- N-alkyl-carbamoyl -- |
| Col. 73, line 18 | Delete " 4- " and substitute -- 5- -- |
| Col. 73, line 26 | After " 4 " insert -- - -- |
| Col. 74, line 31 | Delete " alkysulphonyl " and substitute -- alkyl-sulphonyl -- |
| Col. 75, line 18 | After " 5 " insert -- - -- |
| Col. 76, line 35 | After " 4 " insert -- - -- |

UNITED STATES PATENT AND TRADEMARK OFFICE
CERTIFICATE OF CORRECTION

PATENT NO. : 5,071,865
DATED : December 10, 1991
INVENTOR(S) : Beck, et al

It is certified that error appears in the above-indentified patent and that said Letters Patent is hereby corrected as shown below:

Col. 78, lines 42-43    Delete " dialkyamino " and substitute -- dialkyl-amino

Signed and Sealed this

Twenty-sixth Day of October, 1993

Attest:

BRUCE LEHMAN

Attesting Officer

Commissioner of Patents and Trademarks